US010331855B1

(12) United States Patent
Bratton et al.

(10) Patent No.: US 10,331,855 B1
(45) Date of Patent: Jun. 25, 2019

(54) MODULAR PRESCRIPTION APPROVAL SYSTEM

(71) Applicant: Walgreen Co., Deerfield, IL (US)

(72) Inventors: Edward J. Bratton, Deerfield, IL (US); Michael G. Shope, Orlando, FL (US)

(73) Assignee: WALGREEN CO., Deerfield, IL (US)

( * ) Notice: Subject to any disclaimer, the term of this patent is extended or adjusted under 35 U.S.C. 154(b) by 834 days.

(21) Appl. No.: 14/516,214

(22) Filed: Oct. 16, 2014

(51) Int. Cl.
G16H 40/20 (2018.01)
G06F 19/00 (2018.01)

(52) U.S. Cl.
CPC .......... *G06F 19/328* (2013.01); *G16H 40/20* (2018.01)

(58) Field of Classification Search
CPC ........ G06Q 50/22; G06Q 50/24; G06Q 10/10; G06Q 40/08; G06F 19/328; G16H 10/60; G16H 15/00
See application file for complete search history.

(56) References Cited

U.S. PATENT DOCUMENTS

| 5,628,530 | A | 5/1997 | Thornton |
| 5,832,449 | A | 11/1998 | Cunningham |
| 6,249,715 | B1 * | 6/2001 | Yuri ................... G06Q 10/04 700/108 |
| 6,529,892 | B1 | 3/2003 | Lambert |
| 6,859,780 | B1 | 2/2005 | Cunningham |
| 6,978,286 | B2 | 12/2005 | Francis et al. |
| 6,993,402 | B2 | 1/2006 | Klass et al. |
| 7,014,063 | B2 | 3/2006 | Shows et al. |
| 7,020,697 | B1 | 3/2006 | Goodman et al. |
| 8,103,527 | B1 * | 1/2012 | Lasalle .................. G06Q 40/00 705/35 |
| 8,347,295 | B1 * | 1/2013 | Robertson .............. G06Q 10/06 718/103 |
| 8,392,214 | B1 * | 3/2013 | Pinsonneault ........ G06F 19/328 235/378 |
| 8,489,415 | B1 * | 7/2013 | Ringold ................. G06Q 10/10 705/2 |

(Continued)

OTHER PUBLICATIONS

Mekhjian et al., "Development of a Web-based Event Reporting System in an Academic Enviorment ", Journal of the American Medical Informatics Association; Jan./Feb. 2004; 11, 1; pp. 11-18.

(Continued)

*Primary Examiner* — Jonathan Durant
(74) *Attorney, Agent, or Firm* — Marshall, Gerstein & Borun LLP; Randall G. Rueth

(57) ABSTRACT

A system for the automated categorization, research, correction, enhancement, and resubmission of payment rejections for prescriptions, is disclosed. The system is adapted for use across multiple pharmacies connected to a central server with access to various databases containing information about providers, customers, payers and past prescription history. The system reviews the rejections and categorizes them based on various material within the rejection information and on file in the databases. Once characterized, one or more of several routines and subroutines are worked on the rejection to determine any issues that may be resolved prior to resubmission. Where unsuccessful in automatic resubmission, the system executes a prioritization and agent-matching engine to field the rejection to the most efficient resource to overcome it.

20 Claims, 21 Drawing Sheets

(56) References Cited

U.S. PATENT DOCUMENTS

| | | | |
|---|---|---|---|
| 8,781,854 B1* | 7/2014 | Harris, Sr. | G06Q 50/22 705/2 |
| 2002/0143582 A1 | 10/2002 | Neuman et al. | |
| 2003/0074225 A1 | 4/2003 | Borsand et al. | |
| 2003/0125983 A1 | 7/2003 | Flack et al. | |
| 2003/0144884 A1 | 7/2003 | Mayaud | |
| 2003/0167190 A1 | 9/2003 | Rincavage et al. | |
| 2003/0225595 A1* | 12/2003 | Helmus | G06Q 10/063 705/2 |
| 2004/0059600 A1 | 3/2004 | Ball et al. | |
| 2004/0078247 A1* | 4/2004 | Rowe, III | G06F 19/328 705/4 |
| 2004/0088187 A1 | 5/2004 | Chudy et al. | |
| 2004/0148195 A1 | 7/2004 | Kalies | |
| 2005/0033610 A1 | 2/2005 | Cunningham | |
| 2005/0060197 A1 | 3/2005 | Mayaud | |
| 2005/0071193 A1 | 3/2005 | Kalies | |
| 2005/0080651 A1 | 4/2005 | Morrison et al. | |
| 2005/0090425 A1 | 4/2005 | Reardan et al. | |
| 2005/0137912 A1* | 6/2005 | Rao | G06Q 10/10 705/4 |
| 2005/0154627 A1 | 7/2005 | Zuzek et al. | |
| 2006/0098193 A1 | 5/2006 | Rzasa et al. | |
| 2006/0161294 A1 | 7/2006 | Dimaggio et al. | |
| 2007/0100662 A1 | 5/2007 | Suwalski et al. | |
| 2007/0214014 A1 | 9/2007 | Suwalski et al. | |
| 2008/0275723 A1* | 11/2008 | Wiley | G06Q 10/10 705/2 |
| 2009/0319311 A1* | 12/2009 | Mi | G06Q 10/10 705/2 |
| 2011/0029321 A1* | 2/2011 | Rourke | G06F 17/30896 705/2 |
| 2013/0246094 A1* | 9/2013 | Cruise | G06F 19/328 705/2 |
| 2014/0136231 A1 | 5/2014 | Suwalski et al. | |
| 2014/0278466 A1* | 9/2014 | Simmons | G06F 19/3456 705/2 |
| 2015/0154713 A1* | 6/2015 | Diaz | G06Q 40/08 705/4 |

OTHER PUBLICATIONS

The Institute for Safe Medication Practices. ISMP List of Error-Prone Abbreviations, Symbols, and Dose Designations and ISMP's list of high-alert medications. Accessed on Mar. 23, 2009 at http://web.archive/org/web/20050515210418/www.ismp.org/PDF?ErrorProne.pdf and http://web.archive.org/web20050315165646/www.ismp.org/MSarticles/highalert.

* cited by examiner

FIG. 1A

| BD:19351101 PD:0 EN:810014 PX:MEDDPRIME | |
|---|---|
| GP:PDP13697 | NULL |
| Refilled 29 days too soon | NULL |
| REFILL TOO SOON | RTS -- Rx: 0596046 DT: 07-NOV-2013 DS: 30 RD: 30-NOV-2013 |
| Quantity exceeds maximum | Rounding up to dispense full package is allowed. Example: 3 boxes of 100 allowed as 90 day supply |

FIG. 1B

| LAST FILLD 09-29-12 NEXT FILL 12-06-12 DOSAGE CHNG OVRD-USE 4564564564I AUTH #: | Refill Payable on or after 10-04-12 + | | NEXT RFL 1001 112DAYS TO RFL 3LAST FILL 091212 AT YOUR PHARM |

MODULAR PRESCRIPTION APPROVAL SYSTEM

TECHNICAL FIELD

This invention relates generally to systems and methods for pharmacy operations. In the primary example, the present invention relates to a system (and its associated apparatuses and methods of use) for automatically analyzing, correcting or updating, and resubmitting approval requests for payment or partial payment on prescription fills.

BACKGROUND OF THE INVENTION

When a patient receives a prescription from a health care provider, they take the prescription to their pharmacy to be filled (or it may be faxed ahead in advance). Once the pharmacy receives the prescription, and prior to it being filled, it is typically submitted for approval by the customer's insurance. In this manner, assuming that the insurance approves the prescription, the pharmacist only charges the customer the amount of their co-pay, or whatever other amount remains after insurance pays its portion.

However, this process often does not run smoothly. If the prescription is rejected by the insurance (or other third party payer), the pharmacy will have to collect the entire amount for the prescription from the customer or attempt to overcome the rejection. Because pharmaceuticals are often very expensive (as are insurance premiums), customers will want their insurance to pay its share whenever possible. In some cases, the customer may forego the prescribed medication where insurance rejects it. Thus, efforts are made to try to overcome the rejection. Traditionally, this involves the pharmacist taking time to review the prescription, fix any obvious errors, and resubmit the information for approval. However, the pharmacist may have limited access to information needed to identify and/or correct errors. If their attempts fail, they may have to call the insurer directly. These activities take considerable time, have an unacceptable success rate, and slow down the service provided by the pharmacy.

Prescription formats and details vary, as do the requirements and protocols of the various different payers (insurers and other third parties), which leads to rejections. Rejections come in various formats, but typically have three components: a rejection message, an "additional message" and notes. This information ideally informs the pharmacy as to the reason for the rejection and what needs to be done to fix it. However, it is often missing information that must be acquired from various sources—some within the pharmacy and some outside of it. Attempting to correct these rejections and resubmit for approval is a drain on pharmacists and their staff, result in customer dissatisfaction through longer wait times and the like. Also, there is no systematic or logic-based methodology for addressing rejections, tracking prescriptions and attempts to correct them through the system, or learning from past errors. There is a need for a system that organizes, automates, and enhances/improves existing processes for handling payment requests on pharmacy prescriptions to help streamline the overall prescription fill process and free up pharmacists to perform their primary tasks.

SUMMARY OF THE INVENTION

The present invention provides valuable improvements over the prior art, which are particularly useful to an organization operating a multi-venue chain of pharmacies that have access to one or more centralized (or local) repositories of data that can be used by an automated system to help enhance and cure any perceived defects in a prescription in order to get it approved for filling by a third party payer. The system vastly reduces the amount of time and effort it takes to deal with a variety of different potential rejections, which in turn decreases fill time and improves customer satisfaction. It also improves the success rate of overcoming payment rejections, categorizes rejections based on type and priority, and routes them to the proper system component for resolution.

In a particular embodiment, the present invention provides a prescription approval system for automatically researching, correcting and resubmitting a rejection of a prescription by a payer comprising a first payer server for generating the rejection of the prescription; a prescription approval system server for receiving the rejection from the first payer server, the prescription approval system server comprising a categorization engine for assessing the rejection to determine a rejection category indicative of resolution steps to be taken; and a resolution engine for executing the resolution steps to modify and resubmit the prescription to either of the first payer server or a second payer server; and, a prescription approval system database for housing data for the prescription that includes a summary of actions taken by the prescription approval system with respect to the prescription.

In another embodiment, the present invention provides a prescription approval system implemented across a plurality of pharmacies, each pharmacy having at least one prescription entry device connected to a central prescription approval system server, and wherein the central prescription approval system server is further connected to a plurality of payer servers, each payer server associated with a separate payer entity, said prescription approval system comprising a categorization engine operated by the central prescription approval system server to receive and categorize a rejection of a prescription from a payer server from among the plurality of payer servers, the rejection comprising a rejection code and message content; a resolution engine operated by the central prescription approval system server for executing automated steps to correct the rejection, wherein said steps depend on a rejection category selected by the categorization engine; and a prescription approval system database for housing data indicative of steps previously taken by the resolution engine in an attempt to obtain approval of the prescription.

In yet another embodiment, the invention teaches an automated method of overcoming a payment rejection of a prescription by a first payer comprising the steps of electronically receiving the payment rejection from a first payer server using regular expressions to analyze message content within the payment rejection; accessing a prescription database to gather additional information related to the prescription; using the additional information and the message content to determine category for the payment rejection; executing a first series of automated steps based on the category; executing a second series of automated steps based on the result of execution of the first series of automated steps; wherein execution of the second series of automated steps results in the prescription being submitted to a second payer.

In still another embodiment, the invention comprises an automated system for updating and resubmitting a rejected prescription comprising a central prescription system server for receiving a rejection of a prescription from a payer server associated with a first payer, wherein the prescription comprises a rejection code and an additional message and the central prescription server interprets the additional message to determine a rejection category. The system further comprises a prescription database and a prescriber database accessible by the central prescription system server to obtain information used to assist with determining the rejection category, the information identifying a potential error with prescriber data in the prescription and, in response thereto, the central prescription system server selecting a fax template, populating the template with data from the prescription, and causing the fax to be sent to a prescriber identified in the prescriber database.

In still another embodiment, the invention teaches a prescription updating and resubmission system comprising a prescription input device located at a pharmacy, the prescription input device having a transmitter for transmitting prescription data to a payer server, a central prescription approval server for receiving a rejection of the prescription from the payer server, wherein the rejection includes first information indicative of a reason for the rejection, and a prescription database accessible by the payer server and housing data indicative of any prior steps taken by the central prescription approval server relative to the prescription; wherein the central prescription approval server analyzes the first information to determine a rejection category and, based at least in part on the rejection category, verifies that the prescription database does not indicate that an override step has been performed by the central prescription approval server on the prescription, and if not, adds second information to the prescription indicating an override code and resubmitting the prescription for payment to the payer server.

In still another embodiment, the invention includes a computer readable medium housing a category engine for receiving a rejection of a prescription from a payer server, analyzing the rejection in combination with information relating to the prescription retrieved by the category engine from a prescription database, and determining a category indicating the prescription was submitted prematurely, and a resolution engine for determining an allowable days supply for a medication prescribed by the prescription, determining a days supply a patient identified in the prescription should have based on information in the prescription database, computing a time when the prescription should be resubmitted, and scheduling the prescription for automatic resubmission.

In still another embodiment, the invention includes a computer readable medium housing a category engine for receiving a rejection of a prescription from a payer server, analyzing the rejection in combination with information relating to the prescription retrieved by the category engine from a prescription database, and determining a rejection category, a resolution engine for accessing a prescription database to determine the number of times the prescription has previously been rejected and, if the number exceeds an amount designated by a pharmacy that originally submitted the prescription, forwarding the rejection to a prioritization engine housed within the computer readable medium, wherein the prioritization engine determines a priority for handling the rejection based at least in part on the rejection category.

In still another embodiment, the invention includes a method of allocating a rejected prescription to a particular agent for handling, the steps of the method comprising: receiving at a pharmacy a prescription identifying a patient and a patient address that further identifies a state; adding a designator to the prescription that identifies the prescription and the pharmacy; submitting the prescription to a payer identified in plan data associated with the patient; receiving to a prescription approval server a rejection of the prescription by the payer; determining a rejection category based on first information within the rejection and second information retrieved from a prescription database; verifying that the prescription has not been previously addressed by a particular agent; and, if not, routing the prescription to an agent selected based on at least the state, the payer, and the rejection category.

In still another embodiment, the invention includes a prescription approval system comprising: a central approval server for receiving, categorizing, enhancing and resubmitting prescriptions rejected by one or more payer servers; a first store computer associated with a pharmacy, the first store computer connected to the central approval server and operable to establish first defaults for the central approval server for use in determining automated steps to perform on rejected prescriptions originally submitted by the pharmacy; and a prescription database connected to the central approval server for storing the first defaults along with other defaults relating to a plurality of other pharmacies; wherein the first defaults include first instructions identifying the number of times the central approval server may attempt to resolve rejections relating to a prescription and second instructions identifying a price threshold indicating when a prescription should not be resubmitted to a payer.

In yet another embodiment, the invention involves a prescription resubmission system comprising: a category engine housed on a computer readable medium, the category engine configured to receive a rejection of a prescription and analyze message content stored therein in combination with prescription data relative to the prescription retrieved from a prescription database, and for determining a rejection category based on the analysis; and a resolution engine housed on the computer readable medium configured to reduce the days of supply of a medication prescribed by the prescription based on the rejection category and an analysis of data retrieved from at least a third party database regarding the medication, and for resubmitting the prescription to a payer server.

In still another embodiment, the invention teaches a method for modifying a prescription that has been rejected by a payer, the method comprising the steps of: electronically submitting a prescription to a payer using a prescription entry device, wherein the prescription prescribes a first medication and identifies a patient; receiving from the payer a rejection of the prescription, the rejection containing a rejection code suggesting that the first medication is not covered by a plan through which the payer is obligated to pay for medications for the patient; interpreting, by a categorization engine at a central server, the rejection code and gathering additional data to determine a reject category indicating the first medication is not covered by the plan; accessing a remote database by a resolution engine at the central server to identify a generic equivalent for the medication; replacing the medication with the generic equivalent in the prescription; and, resubmitting the prescription to the payer.

In yet another embodiment, the invention includes a prescription updating and resubmission system comprising a prescription input device located at a pharmacy, the prescription input device having a transmitter for transmitting prescription data to a first payer server associated with a first payer, a central prescription approval server for receiving a rejection of the prescription from the first payer server, wherein the rejection includes first information indicative of a reason for the rejection, and a prescription database accessible by the payer server and housing data indicative of any prior steps taken by the central prescription approval server relative to the prescription; wherein the central prescription approval server comprises a category engine for determining a rejection category based on at least the first information, and a resolution engine for automatically obtaining data to assess and correct the prescription based on the rejection category, wherein the resolution engine determines to submit the prescription to a second payer server associated with a second payer, and wherein the resolution engine further updates a patient records database to add information about the second payer and delete information about the first payer.

While certain embodiments are mentioned above, numerous other embodiments, systems, methods, features, and advantages of the present invention will be, or will become, apparent to one having ordinary skill in the art upon examination of the following drawings and detailed description. All such additional systems, methods, features, and advantages included within this description, are within the scope of the present invention, and may be included in one or more of the accompanying claims. Though a multi-venue pharmacy with a centralized processing center and database structure is used for describing the primary example discussed in the written description below, one of skill in the art will recognize that the prescription approval system could also be adapted for use with a single venue, or multiple venues each having separate data storage capabilities.

BRIEF DESCRIPTION OF THE FIGURES

The invention can be better understood with reference to the following figures. The figures are provided to help illustrate the principles of the present invention, and are not intended to be limiting. For example, though the disclosure includes various flow charts setting forth a certain ordinate step of performing tasks within the system, one of skill in the art will recognize that the system could operate by practicing the steps in various different orders, and that order of operation is not considered a part of the invention unless specifically claimed. Where like numbers are used to identify or designate steps in flowcharts, those steps are generally identifying the same activities being taken across different flow charts. For example, where two separate processes may result in the same step being taken, that step may be identified with the same designation number on two different flow charts, one representing the first process and one representing the second process.

FIG. 1A is a first sample of prescription rejection information received from a third party payer;

FIG. 1B is a second sample of prescription rejection information received from a third party payer;

Figure 2:
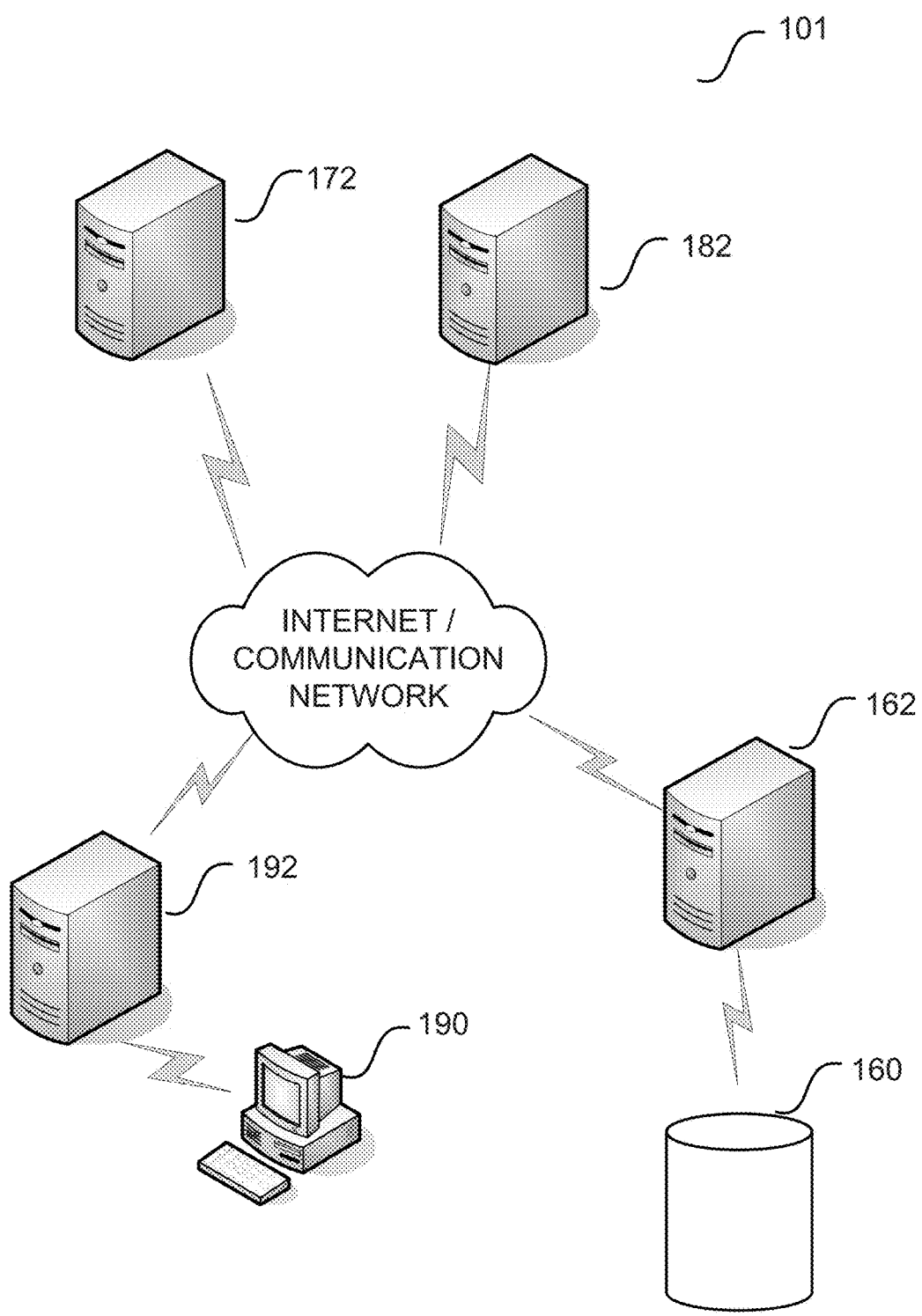
FIG. 2 is a system diagram illustrating an embodiment of a computer networked prescription approval system in accordance with the invention.

Illustrative and exemplary embodiments of the invention are described in further detail below with reference to and in conjunction with the figures.

DETAILED DESCRIPTION

The description that follows describes, illustrates and exemplifies one or more particular embodiments of the present invention in accordance with its principles. This description is not provided to limit the invention to the embodiments described herein, but rather to explain and teach the principles of the invention in such a way to enable one of ordinary skill in the art to understand these principles and, with that understanding, be able to apply them to practice not only the embodiments described herein, but also other embodiments that may come to mind in accordance with these principles. The scope of the present invention is intended to cover all such embodiments that may fall within the scope of the appended claims, either literally or under the doctrine of equivalents.

The Prescription Approval System (or "PAS" for short) described herein has several components and affects several different entities. For simplification, the description that follows attempts to use common names for these entities, which should be broadly construed to cover different uses of the system. The term "prescription" refers generally to a medical prescription that is to be filled by a pharmacy. Each prescription is uniquely identified in various ways, but at least by a unique prescription identification number or "PIN" assigned by the system or by the pharmacy. Generally, the specification discusses managing and processing of payment rejections for prescriptions. Thus when a "rejection" is being discussed, it will be understood to be a payment rejection of a prescription.

The term "store" or "pharmacy" refers to an individual pharmacy location or venue within the system, and particularly, the location where the prescription in question has been sent to be filled. Because the system allows for flexibility such that individual stores may tailor their use of it, the specification may identify a "first store" and a "second store" so as to distinguish them from each other.

The term "customer" or "patient" refers to the person who has been prescribed medication or treatment by the prescription in question. The person is a "customer" of the pharmacy, but a "patient" of the health care provider that issued the prescription. Unless stated otherwise, "customer records" and "patient records" synonymously refer to the electronic records maintained by the pharmacy as to that particular customer.

The term "prescriber" refers to the physician, nurse practitioner, or other properly licensed healthcare provider that issued the prescription in question. Generally, the term prescriber refers to an individual person that authorized the prescription, but it may refer to the related healthcare organization or entity for whom that individual person was performing services in certain instances.

The term "third party payer" or simply "payer" refers to an entity to which the prescription is submitted for payment authorization. Typically, the payer is the primary healthcare insurance provider of the customer, but it may alternatively be an agency such as Medicare or some other government organization, a pharmacy benefits manager, a prescription savings club, a corporation, a pre-paid card or discount card management agency, or an intermediary benefits management agency such as that administers healthcare-based aspects of a cafeteria plan. Typically, in order to allow for ideal system interaction, each payer will be set up to either approve or reject a prescription request electronically, and in the latter case, will submit the rejection information in a system-recognized, standard format.

FIG. 1 shows an example prescription rejection 10 and components of rejections that the PAS works with to remedy. In accordance with common formats, each rejection 10 is comprised of three components: a rejection code 20, a processor message 30, and an additional message 40. This format is not required, but is used by the generally accepted, and widely used intermediary data service (Relay Health) that helps transmit data relating to prescriptions between the pharmacy and the payer (and others). Data services such as Relay Health do not change the data in any way. They merely route it between the store and the designated payer. The rejection code 20 is typically in a standardized format, and is comprised of a series of letters and numbers. These letters and numbers will uniquely identify the prescription ID (such as by the store-assigned prescription identification number or PIN), as well as provide a code that represents the type or reason for the rejection. Unfortunately, different payers use these codes to identify different things, or they may vary by state and other variables. Accordingly, the reject code is not necessarily a reliable indicator of the category or type of the rejection.

The other components of the rejection are not standardized. Rather, they are free-form boxes that may not even be filled in, or may contain any variety of text. In the example provided, the processor message 30 is indicating two potential errors with the prescription: (1) the refill was requested before the current supply of medication should be running low; and (2) the quantity of medication requested is over some pre-determined limit set by the payer (or by some regulatory body, etc.). Where the information is this specific in the processor message, the system can generally accept it as a category and quickly route to the necessary sub-routine for correction or resolution. But that is not always the case. The processor message field 30 within a rejection is character limited. Accordingly, there is an additional message field 40 for expansion if needed. Here, the additional message field is informative and provides information necessary to correct the rejection. But again, that is not always the case. Elements 41-44 are each examples of additional messages from different rejections. Not surprisingly, as shown in element 43, the additional message field may be blank. The format and meaning of other messages may vary widely by payer. Accordingly, one benefit of the system, as discussed below, is its ability to "learn" by tracking its actions taken on different rejections from different payers. The system's historical database will develop information over time corresponding to a particular payer that will assist in identifying what the messages mean, and also what steps worked and did not work to resolve them in the past.

From a computer hardware standpoint, the PAS utilizes and or interacts with various computer and database elements in order to perfect and get approval of prescriptions. FIG. 2 provides a map of certain of these hardware elements, where the elements on the lower half of the diagram are associated with the pharmacy (or multi-store pharmacy system), and the elements on the upper half of the diagram are associated with external resources. As shown, store computer 190 would be, for example, a primary entry and fill computer within a particular pharmacy. Computer 190 could be any computerized device capable of data entry for purposes of submitting a prescription for approval (input) or receiving payment authorization (as output). For example, it could be a handheld scanning device, a tablet, a laptop, a desktop, or the like. Depending on the size of the computer 190, it may be connected to a store server 192 that has additional memory and computing capacity to help drive and operate components of the PAS. While that embodiment is shown, in other scenarios the computer 190 may send the request (or receive the request) directly through the network.

As shown, "the network" is the internet. However, proprietary and secure closed systems for remote connection between the hardware elements could be used. In any event, the network connects the store server 192/store computer 190 to a central PAS server 162 in the illustrated embodiment. The PAS server 162 houses the majority of the software engines described below, and has access to the PAS database 160 that houses historical information about patients, payers, prescriptions, actions taken on rejections, and other information as described below. The PAS leverages the information in this database 160 in order to determine next steps and actions for correction and resubmission on rejected prescriptions. These servers may be of various known constructions, such as, for example, an IBM System x3650 M3 rack server. The actual server size and capability will vary depending on their intended utilization. For example, the individual store servers 192 see much less traffic than the centralized PAS server 162, and, accordingly, may be scaled down in size and functionality as appropriate.

In some embodiments, the PAS may be adapted to run directly from a single store, without use of a central PAS server. In this case, the PAS database 160 would connect to the store server 192. However, the PAS is more powerful and performs better based on the more rejections it handles and learns from. Accordingly, it is most efficient to operate in a networked scenario where one pharmacy can learn from rejections received and resolved by another pharmacy. Accordingly, there may be dozens, hundreds, or even thousands of store computers 190/store servers 192 that are connected to the PAS system server 162.

External to the pharmacy network is the payer server 172 and other third party server 182. As with the store server 192, the image of one server is merely for convenience. In reality, there may be dozens or hundreds of payer servers 172 that can be accessed by PAS server 162 for submission of a prescription. The particular payer server to which a prescription is sent will depend on information within the store computer 190 (or perhaps the PAS database 160) regarding the patient. For example, a patient database file will typically have insurance plan information on the patient. The PAS will recognize the insurance provider and will associate that payer with a particular DNS associated with a payer server 172 for routing of the prescription for approval. As discussed below, where this plan information is incorrect or outdated, the PAS may be able to self-correct and re-direct the prescription.

Other third party server 182 generally represents any computer system or data repository accessible by the PAS that is not connected with a payer or store. This server 182 could represent, for example, a provider database used to maintain information about providers that could be used by the PAS to correct a provider's name, a drug database that stores proper NDC (national drug code) identifications in cases where there is a potential mistake with the prescribed medication, or, in the case of larger institutional health system providers, a hospital or health system database. While some information related to patient medical records will not be available to the PAS, much of the information that it utilizes is maintained by state or government agencies. For example, the listing of NDCs to identified medications that may be fit for prescription is updated daily by the Federal Drug Administration (FDA). This listing, or information within the database, may also provide generic alternatives, proper dosing information, etc. The Department of Health and Human Services maintains a daily-updated registry of providers, listed by 10-digit National Provider Identifiers, or NPIs. This information can be accessed and used by the PAS to correct provider information in a rejected prescription.

The elements shown in FIG. 2 are obviously all computer elements of the system that are used when a rejection is handled in a completely automated fashion by the PAS. However, the PAS will not be able to resolve all rejections through automation. For example, there may not be enough information in the processor and additional messages to allow the PAS to properly route and act upon a rejection. In other cases, a rejection may have failed to be resolved through automation after multiple attempts. In these types of scenarios, where a store authorizes it, the PAS may route the rejection to a central Resolution Center. The Resolution Center has human agents that review all notes of attempts to automatically resolve the rejection by the PAS and determine next steps from there. However, instead of simply a first in-first out system of operation at the Resolution Center, the PAS operates to prioritize and match the prescription rejection to a specific agent best capable to resolve the rejection in a timely fashion based on, for example, the nature of the rejection and the agents' particular expertise, as discussed more fully below.

Collectively, all of the servers, desktops, and smartphones are understood to be general purpose computers; however, at least the PAS server 162, store server 192, and store computer 190 are equipped with special applications or software to perform its function as a component of the PAS 100, thus converting them to special purpose machines. For example, to operate within the system, a store computer 190 may have special PAS software for use in interacting with the PAS server 162. For its part, the PAS server 162 contains various specialized software engines, as discussed below, to facilitate various aspects of the system.

The connectors of FIG. 2 illustrate how information flows between the various hardware devices that work in association with the PAS 100 according to the illustrated embodiment. Though everything connects through the internet as shown, it is preferred that traffic between any two illustrated components be routed through the PAS server 162. This allows for a common user interface at the PAS server 162 for handling all PAS traffic, prevents unnecessary traffic from encumbering store servers 192, enhances overall data security to backend systems, and allows for more thorough and controlled population of the centralized PAS database 160. More will be explained as to the interaction between these various system components in association with various flow charts discussed below.

Figure 2A:
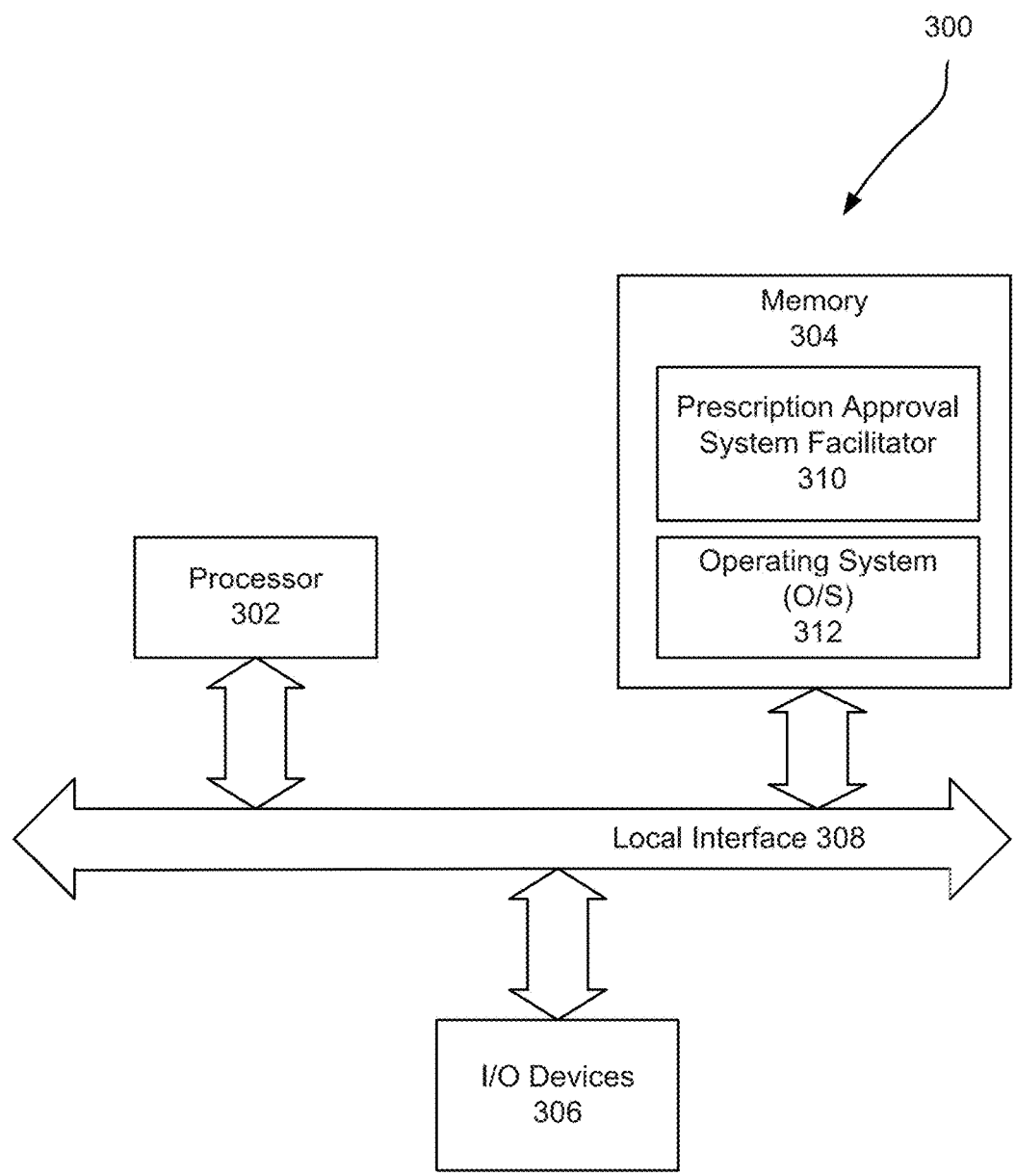
FIG. 2A is a schematic diagram of certain aspects of a computer that might serve as a component of the prescription approval system of FIG. 2.

Now referring to FIG. 2A, a schematic diagram of an exemplary store computer 190 is provided. The computer includes an interactive hardware portion and a software portion. The interactive hardware portion can include an input/output device 306, such as a credit card readers, input modules for PLCs, a keyboard, mouse, microphone, touch screens, interfaces for various devices, barcode readers, stylus, laser readers, radio-frequency readers, etc. The touch screen can be a liquid display crystal (LCD), display screen, a plasma screen, a light emitting diode (LED), or any other screen capable of displaying text and images. Furthermore, the I/O device 306 may also include output devices, including, but not limited to, receipt dispensers, output modules for PLCs, a printer, barcode printers, displays such as touch screen displays, etc. Finally, the I/O device 306 may further include devices that communicate both inputs and outputs, for instance but not limited to, a modulator/demodulator (modem; for accessing another device, system, or network), a radio frequency (RF) or other transceiver, a telephonic interface, a bridge, and a router.

The hardware portion also includes a central processing unit (CPU) portion or processor 302 (i.e., a microprocessor), and a local interface 308. The software portion comprises a memory 304. The processor 302 can be any computer-processing unit from a singular microchip to extensive microchip configurations. The memory 304 can include, without limitation, any one or a combination of volatile memory elements (e.g., random access memory (RAM, such as DRAM, SRAM, SDRAM, etc.)) and nonvolatile memory elements (e.g., ROM, hard drive, tape, CDROM, etc.). Moreover, the memory 304 may incorporate electronic, magnetic, optical, and/or other types of storage media, and can have a distributed architecture where various components are situated remote from one another, but are still accessed by processor 302. The interactive hardware portion is coupled to the processor 302 and memory 304 by the local interface 308 such that a command entered by a user or customer through the interactive hardware portion will be forwarded to the processor 302 and then to memory 304.

The processor 302 can be any custom made or commercially available processor, a central processing unit (CPU), an auxiliary processor among several processors associated with the computer 190, a semiconductor based microprocessor (in the form of a microchip or chip set), a macroprocessor, or generally any device for executing software instructions. Examples of suitable commercially available microprocessors are as follows: a PA-RISC series microprocessor from Hewlett-Packard Company, an 80x86 or Pentium series microprocessor from Intel Corporation, a PowerPC microprocessor from IBM, a Sparc microprocessor from Sun Microsystems, Inc., or a 68xxx series microprocessor from Motorola Corporation. The processor 402 may also represent a distributed processing architecture such as, but not limited to, SQL, Smalltalk, APL, KLisp, Snobol, Developer 200, MUMPS/Magic.

The memory 304 can include or store an executable program such as PAS facilitator 310, and an operating system 312. Other executable programs may include a touch screen interface application, and a wireless network communication software application such as a common browser like Internet Explorer. Various other executable programs may also be stored in memory 304 that are unrelated to the present invention. The executable programs can be implemented in software, firmware, hardware, or a combination thereof. Applications stored in memory 304 may be a source program, executable program (object code), script, or any other entity comprising a set of instructions to be performed. When a source program, the program needs to be translated via a compiler, assembler, interpreter, or the like, which may or may not be included within the memory 304, so as to operate properly in connection with the O/S 416. Furthermore, each application can be written as (a) an object oriented programming language, which has classes of data and methods, or (b) a procedural programming language, which has routines, subroutines, and/or functions, for example but not limited to, C, C++, Pascal, Basic, Fortran, Cobol, Perl, Java, and Ada.

The operating system 312 essentially controls the execution of other computer programs, such as the PAS facilitator 310. A non-exhaustive list of examples of suitable commercially available operating systems is as follows: (a) a Windows operating system available from Microsoft Corporation; (b) a Netware operating system available from Novell, Inc.; (c) a Macintosh operating system available from Apple Computer, Inc.; (d) a UNIX operating system, which is available for purchase from many vendors, such as the Hewlett-Packard Company, Sun Microsystems, Inc., and AT&T Corporation; (e) a LINUX operating system, which is freeware that is readily available on the Internet; (f) a run time Vxworks operating system from WindRiver Systems, Inc.; or (g) an appliance-based operating system, such as that implemented in handheld computers or personal digital assistants (PDAs) (e.g., PalmOS available from Palm Computing, Inc., and Windows CE available from Microsoft Corporation).

When the store computer 190 is in operation, the processor 302 is configured to execute software stored within the memory 304, to communicate data to and from memory 304 and to generally control operations of store computer 190 pursuant to the software. The PAS facilitator 310 and the operating system 312, in whole or in part but typically the latter, are read by the processor 302, perhaps buffered within the processor 302, and then executed. When the PAS facilitator 310 is implemented in software, it can be stored on any computer readable medium for use by or in connection with any computer related system or method. The PAS facilitator 310 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions.

In the context of this document, a "computer-readable medium" can be any means that can store, communicate, propagate, or transport the program for use by or in connection with the instruction execution system, apparatus, or device. The computer readable medium can be for example, but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). In another embodiment, where the PAS facilitator 310 is implemented in hardware, it can be implemented with any, or a combination of, the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

While the memory and CPU descriptions above were described in reference to a store computer 190, it will be understood that the other hardware elements depicted in FIG. 1 will also have similar processors and memories that operate along similar parameters and in similar or identical ways. The memory element on the PAS server 162 will have the primary component of the PAS facilitator 310 stored therein, which will contain the various engines discussed below. Collectively, it will be understood that the PAS facilitator 310 is the software existing on the various hardware devices that is specially programmed and uniquely tailored to convert the general purpose computers discussed in association with FIG. 2 into special purpose computers fit to operate the PAS 100.

The PAS facilitator 310 resident on the PAS server 162 comprises several modular software engines that are generally referred to herein as Categorization Engine 315, Resolution Engine 320, Prioritization Engine 330, and Agent Matching Engine 340. The PAS may use each of these engines in the processing of a particular prescription rejection. At a very high level, when a rejection is received by the PAS, it is routed to the Categorization Engine 320 which analyzes it and attempts to categorize it. If successful, it is then routed to the Resolution Engine 330, which performs operations to overcome the rejection and resubmit the prescription for payment based on the output of the categorization engine. If the Resolution Engine is not able to correct the rejection, depending on preferences at the relevant store, the rejection may pass through the Prioritization Engine 330 where it is assessed relevant to other unresolved rejections and then through the Agent Matching Engine 340 that aligns it with a particular agent at the resolution center. If a store is not supported by the resolution center, and in the event that a rejection remains unresolved after operation by the PAS, only then is it returned to the store for final resolution. Such final resolution generally involves requiring full price from the customer since no payer has approved payment.

To discuss operations of the various engines, and particularly the Category and Resolution Engines, the attached flowcharts of FIGS. 3-4 and 7-17 will be helpful. It is understood by those of ordinary skill in the art of computer programming that these flowcharts illustrate steps taken by a computer program or module, and that there would be underlying source code that would actually execute the steps and make the determinations set forth. Generating that source code, given the flowcharts and this description as guidance, would be within the capability of one of ordinary skill in the art of software programming, and such a person could generate the code without undue experimentation.

Figure 3:
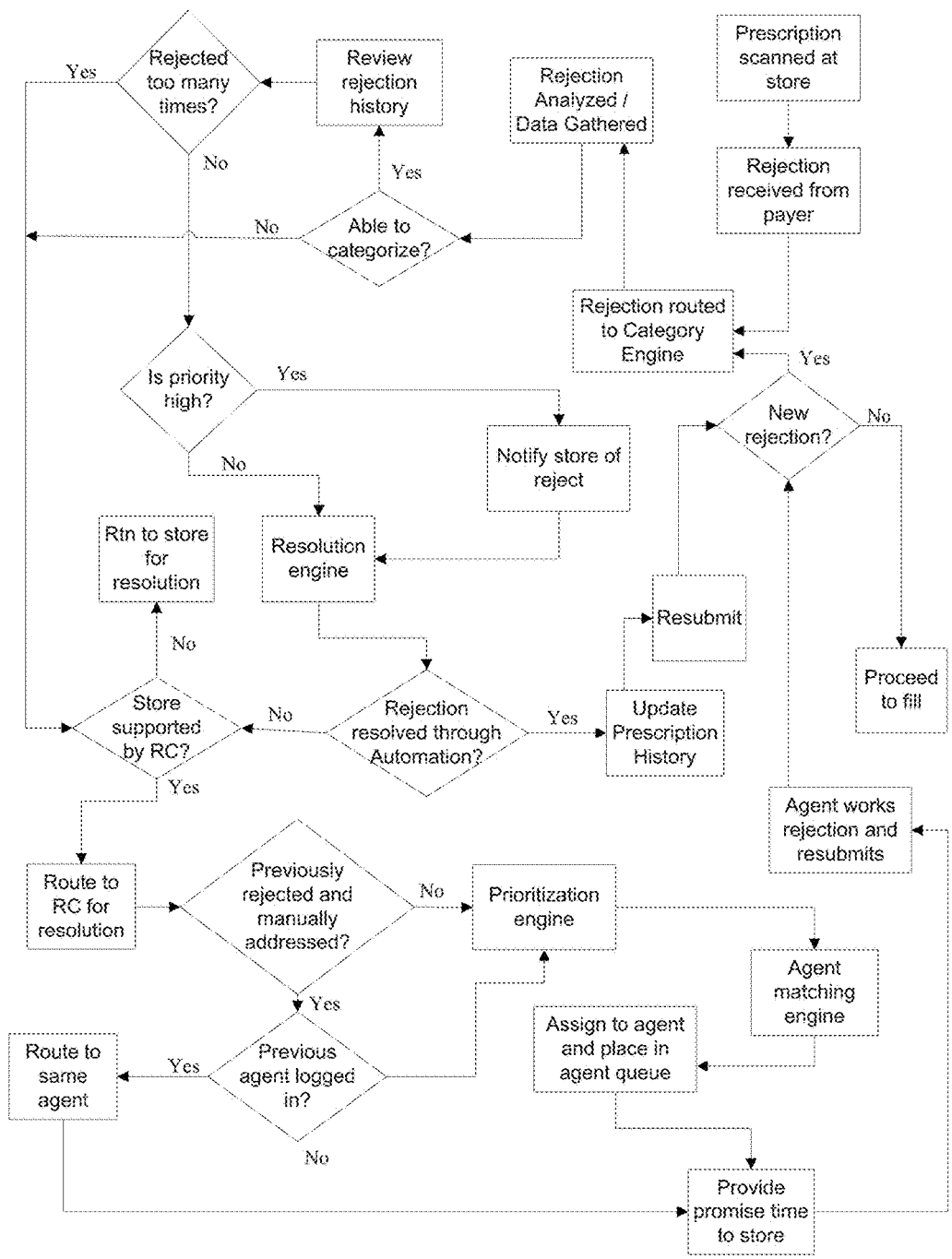
FIG. 3 is a flow chart showing steps taken by the prescription approval system in order to process a prescription, according to certain embodiments.
Figure 4:
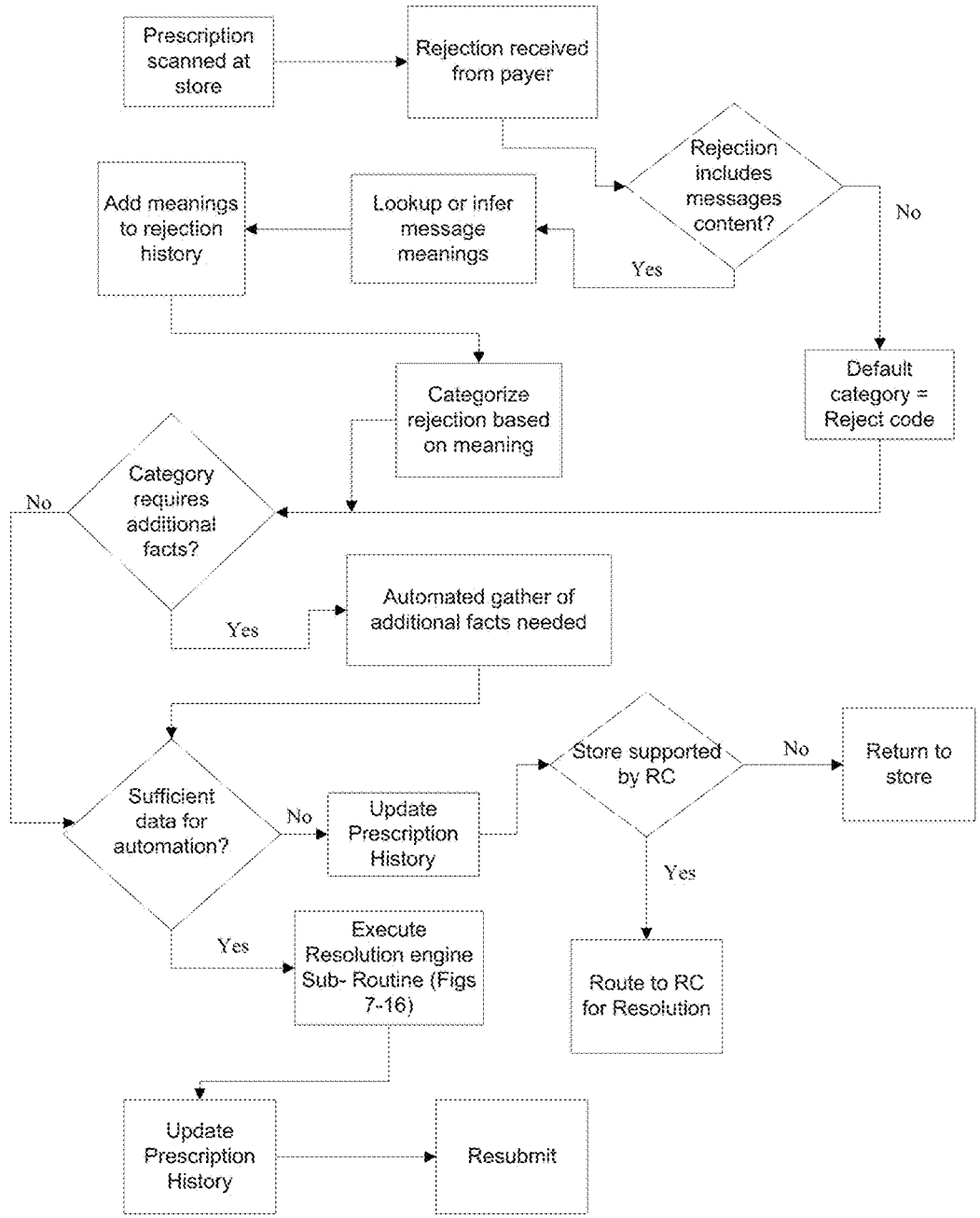
FIG. 4 is a flow chart showing more detailed steps taken by a resolution engine of the prescription approval system, according to certain embodiments.

FIGS. 3 and 4 show a high level view of the PAS at work. The process starts in FIG. 3 at step 200 when a prescription is received by a store (pharmacy) and submitted for payment. This step may be automatic based on a scan of a prescription electronically received, such as via facsimile followed by optical character recognition (OCR), or may be manual based on data entry from a store clerk. Information within the prescription will be entered into fields that will identify the primary payer, which in turn identifies to whom the prescription will be submitted. Other inputs include the patient name, the medication and dosage information, the date, and a PIN. The PIN ideally is a unique identifier for the prescription that includes a unique identifier for the store. For example, in a pharmacy network with hundreds of stores, the PIN might be a three letter designator identifying the store followed by an eight digit number sequentially identifying the prescription, or identifying it by time and date received. This PIN number is submitted with the prescription and remain attached to it, whether accepted by the payer or rejected. Thus, it can be used to track the prescription through the system through subsequent submissions by the PAS if such subsequent submissions are necessary.

Another piece of information submitted with the prescription is a payer. If the submission is automated, the PAS may populate payer information from a store database or the central PAS database 160 based on the patient name. Typically each patient will have a specific pharmacy that they frequent, and that pharmacy will have the patient's health insurance information or other payment plan information on file. If a prescription arrives at a store that is for a customer that has not used the store before, or that does not have any payer information on file, store personnel will have to contact the customer or the prescribing provider to obtain the information and manually fill it in to the proper fields.

Once all of the information is filled in, the prescription is routed to a payer server 172 based on its data. As mentioned above, this may be done by a third party data routing service, such as Relay Health. The payer will then take action on the prescription, based on its own information on hand. This may be automated or manual, depending on the capabilities of the payer. If the prescription is authorized, it is returned to the store with an authorization code and, if applicable, a co-pay or portion that the patient is responsible for. If it is not approved, the payer will issue a rejection in the format described above. Specifically, the rejection will include a reject code, a processor message and an additional message, though some of these fields may be blank. The PAS receives the rejection from the payer at step 205, and, at step 210, routes it to the Categorization Engine (or Category Engine) 315.

The purpose of the Category Engine 315 is to assess the rejection and to direct it to the proper sub-routine within the Resolution Engine 320 based on its category. While there is no set number of subroutines within the PAS Resolution Engine, and new routines could be added as required, several are described below. A subroutine is generally created when there are enough rejections of a particular type that can be addressed with a particular set of actions, and when those actions are amenable to being developed into an automated process. In any event, there is not a 1:1 alignment between PAS categories and prescription reject codes. And, though the reject code within the rejection is helpful, it does not always result in a particular category. There are hundreds of potential reject codes, and payers do not all use them in a consistent manner. For example, a code for "prior authorization required" might mean one thing to a first provider, and another to a second provider. Accordingly, as discussed below, the Category Engine 315 will take into consideration any information on the payer from past rejections bearing the same reject code to determine any alternative or non-standard way in which the payer is known to use the code, and use that to help establish the category.

At step 215, the Category Engine 315 sets to work analyzing and deciphering the information within the rejection. This is an automated process that generally uses Regular Expressions and keyword string manipulation to extract and interpret the information contained therein. Rejections are often filled with "code words" and abbreviations, but the PAS knows what is typical to find in a rejection and where based on past experience. Stored within the PAS database are various keys for helping decipher commonly used abbreviations, and also history about most payers, such that a payer system that uses a certain abbreviation may be easily interpreted by the PAS Category Engine.

In some cases, there is simply not enough information in the rejection to enable proper categorization. When this happens, the rejection is not passed to the Resolution Engine. Instead, it is either routed back to the store at step 250 if the store is not supported by the resolution center, or it is routed to the resolution center. In accordance with FIG. 2, if categorization is possible, the Categorization Engine reviews the rejection history at step 220. This step may, in some embodiments, be done prior to step 215. The rejection history will not be stored within the rejection itself. Rather, it will be stored within the PAS database 215, and can be accessed using the PIN. Put differently, when a prescription is rejected, it comes back as a rejection with the PIN attached for recognition purposes, but it will not come back with any data relating to prior attempts at submission. Thus, the information relating to prior attempts must be stored within the PAS. The rejection history may be used by the PAS in many ways. For example, the history may help the Categorization Engine determine a different category for the rejection. Where one option was tried in the past and failed, provided that there is no new inputs, it will likely fail again. By recognizing this, the PAS avoids the infinite loop phenomenon that continuously submits a prescription and continuously gets the same rejection.

Another method to prevent this is built in to the path of FIG. 3 by assessing how many times the prescription has been rejected. If more than a pre-designated amount (say 5 times), it will not be submitted to the Resolution Engine 320. While this number can be set at any amount, there comes a point where multiple attempts at approval by the PAS have failed and it is better to move the prescription along. The pre-designated amount could be tailored by individual stores such that one store will accept a higher number of attempts by the PAS than others. In other cases, the pre-designated amount may vary based on the category or rejection in question. Where the pre-designated number is recognized to have been exceeded, the prescription is given an automatically high priority and passed to either the resolution center or, if the store in question is not supported by the resolution center, then back to the store at step 250. Any time a rejection is passed back to the store, the PAS provides a full account of the prescription history that shows the attempts and actions that have been taken to attempt approval.

Assuming that the pre-designated number of trips through the PAS have not been triggered, the PAS will then check for a high priority. A high priority may be stored within the prescription history, and may be placed there by the PAS, the store, or the provider. The PAS might make a prescription higher priority if a certain time period has passed since it was first submitted, for example. The store might designate a prescription as high priority if it wants frequent updates on the prescription, or has a demanding customer. The provider might designate the prescription as high priority if the need to administer the medication is urgent. In any event, where the priority is high, the PAS may expedite it through the resolution engine ahead of others. Also, as shown in FIG. 2, a high priority triggers the PAS to notify the store of the reject at step 225 prior to passing the reject to the Resolution Engine at step 230. The notification will provide basic information only, but will serve as a status check Activity by the Resolution Engine is discussed in accordance with subsequent flow charts, but generally the attempts to resolve the rejection are either believed to be successful by the PAS, in which case the process moves to step 240 toward resubmission, or unsuccessful in which case the process moves toward routing the rejection to the store (step 250) or the resolution center (step 251), if supported. In success cases, the prescription is updated and resubmitted to the payer (or to a different payer, based on the outcome of the automated resolution) at step 240. Regardless of the anticipated outcome, the Resolution Engine 320 always updates the PAS database 160 with the actions taken on the prescription, such as in a log format, at step 235. If the operation worked and the prescription comes back approved, then this will be further annotated in the database as a successful remedy for the given scenario (e.g., rejection code, payer, medication type, message content, etc.) should it occur again in a new prescription. If the operation failed and the prescription is again rejected, the history will continue to be updated and this historical evidence will help the PAS operate more effectively the next time through. Failures (e.g., a next rejection is received on the prescription after resubmission) are directed back to step 210 for categorization. Successes (e.g., approval after resubmission) are routed to the store to be filled at step 245.

In cases where the Resolution Engine is to be by-passed, or where the Engine is unable to cure a rejection to the point that resubmission is worthwhile, as mentioned above and shown on FIG. 2, the rejection is either routed to the store (step 250) or to the resolution center. Again, the resolution center is a centralized facility of agents that can manually address problem rejections. However, all stores are not necessarily able to work with the resolution center due to certain state laws regarding handling of healthcare related information by people outside the state. In states that have such laws, typically the stores cannot utilize the benefits of a centralized resolution center. Because the store will be identified within the PIN, the PAS will be able to determine if the store is supported by the resolution center. In that case, the PAS will again look to the history of the rejection to see if it has already passed through the resolution center, and, if so, will assign it a high priority and route it to the same agent that handled it before at step 270, assuming that agent is available. If the agent is not available, or if the prescription has not yet passed through the resolution center, the PAS will pass the rejection to the Prioritization Engine at step 255. The actions of this Engine will be discussed further below. Once prioritized, the rejection passes to the Agent Matching Engine 340 at step 260. This engine uses various data to match the rejection to a specific agent, as discussed below. The agent is assigned and the rejection is queued with the agent at step 265.

Once the rejection is queued to an agent, the PAS delivers a promise time to the store based on data received from the Prioritization Engine and Agent Matching Engine at step 275. The agent then works the rejection manually at step 280 and resubmits. In some cases, such as where repeated attempts have been tried by the resolution center, or the agent does not believe the prescription can be approved on the present information, the rejection will be sent back to the store with notes from the resolution center on what is needed, or instructions to bill the client for the full amount (i.e., no payer is available).

While FIG. 3 provides an overview of the entire process at a high level, FIG. 4 focuses more on the activities at the Categorization Engine 315. Again, the process starts with submitting the prescription and receiving a rejection. If the rejection comes back without any details in the processor message or additional message fields, there will be nothing for the Categorization Engine to use except for the reject code and possibly the history on the prescription stored in the PAS database, if any. In this case, the Category Engine may be programmed to accept the reject code and place the rejection in category assigned to that reject code at step 405. However, as mentioned, this often results in error and may lead the Resolution Engine down the wrong path. Where there is information in the fields, regardless of the reject code, that information is analyzed at step 410 in case there is a more appropriate category than what the reject code suggests.

Message meanings may be "looked up" from the PAS database or from one of the various third party servers 182 discussed above. It can also be "inferred," such as from past experience with the particular payer or other empirical data retained within the PAS database such that the PAS learns inferentially over time and corrects its mistakes. Regular expressions and other known raw data analysis techniques can only do so much. For example, these techniques may extract a resubmit date that might yield a string of numbers that actually contains two dates: 010314020814. The PAS may know the date it is looking for is the second one, Feb. 8, 2014. In this example, the string needs to be processed further to produce this actual date using a special set of rules for post processing logic. For example, it may identify that the first date is in the past, so the reject code identifying that the prescription was submitted too soon cannot be accurate.

This is one of many examples of how inferential analysis is used by the Category Engine to properly fill in the meaning of and "enhance" the data within the rejection at step 415. Once the meaning is enhanced as much as possible or fruitful, a category is selected at step 420.

Based on this category selection, some additional facts may be required prior to submission to the Resolution Engine. Because the Category Engine is tied to the Resolution Engine, it knows what inputs are required to work the sub-routine that will result from the category selection. Where this material is missing, the Category Engine will attempt to acquire it at step 425, such as from a provider database, government database, the PAS database, etc. If successful, the rejection is then passed to the Resolution Engine for automated resolution at step 230. If it is unsuccessful, the rejection is either passed to the store (step 250) or to the resolution center (251). In either event, the PAS always updates the PAS database as to what actions were taken relative to the PIN at step 235.

Like the Category Engine, the Resolution Engine "learns" inferentially. Specifically, it determines outcomes in part by use of the historical data in the PAS database on how similar issues (patient, drug, plan, wording, etc) were resolved successfully in the past, and the final step is always to update the logical data model of the PAS database so that it continues to be more effective at troubleshooting. Every step the PAS performs is tracked and recorded for use in audit, problem-solving, and to avoid duplication of unsuccessful steps. The PAS may record not only the steps taken, but also may enter automated comments (e.g., the response to its steps). The data model is cross-referenced such that it can be used by the resolution engine not just specific to the PIN being worked, but with respect to, for example, all successfully resolved rejections issued from a particular payer with a particular reject code, etc.

Figure 5:
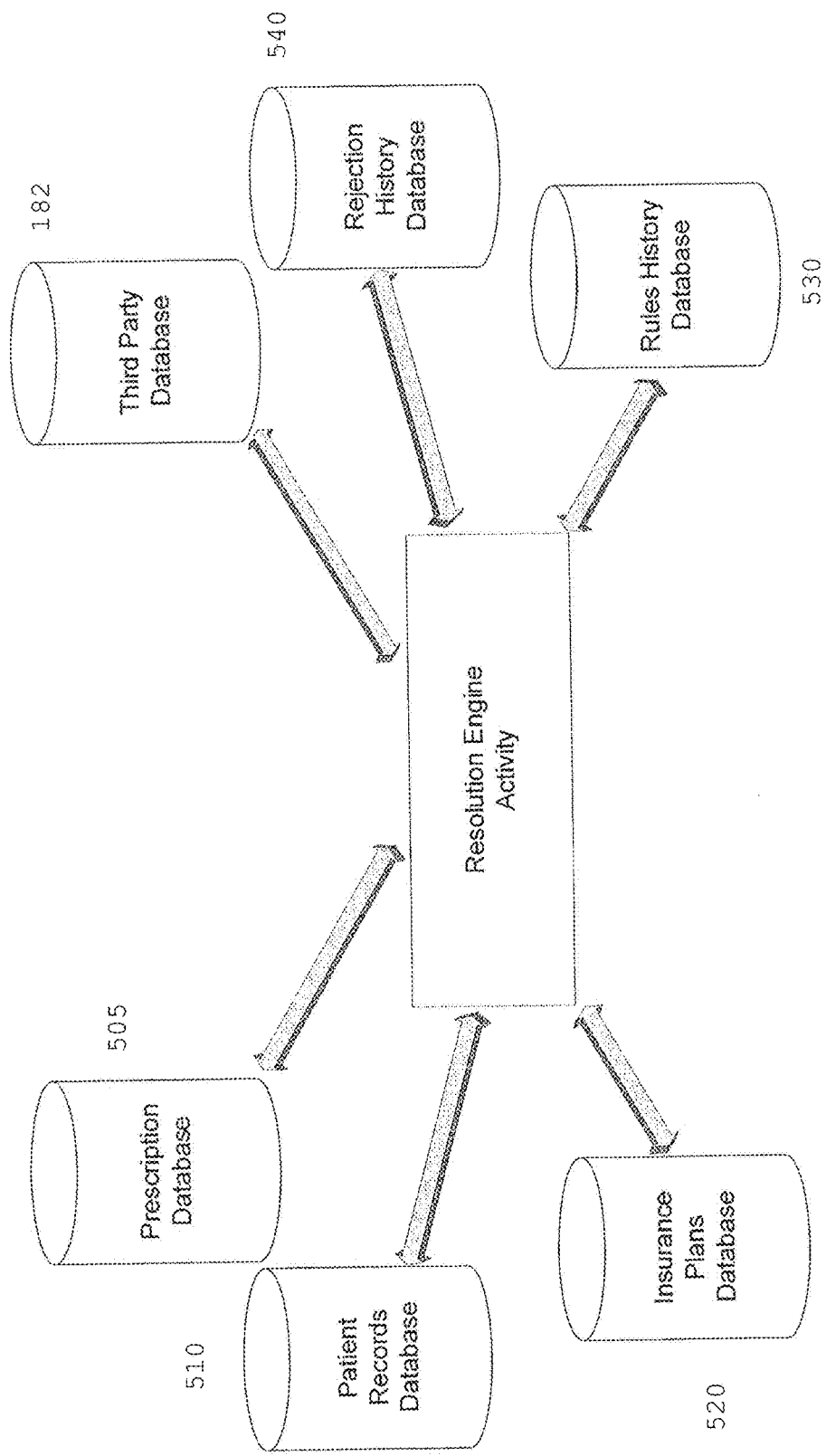
FIG. 5 is a system map showing information repositories accessible by the resolution engine in accordance with the invention.

Though, as shown in FIG. 4, the Category Engine may reach out to the PAS database to fill certain information in known to be required in a particular resolution path, the Resolution paths themselves performed by the Resolution Engine often need more data depending on the results to the resolution steps attempted. Accordingly, the Resolution Engine may have need to access various data sources, as shown in FIG. 5. Though listed as separate databases in FIG. 5, all but the Third Party Database 545 in FIG. 5 may be part of the PAS database 160. Alternatively, they may be stored (and even controlled) separately. The information that the system may derive from the various databases is shown on FIG. 5A. For example, the Prescription Database 505 of FIG. 5 may house the prescription information records 506 identified on FIG. 5A. Fields may be added or subtracted based on the information commonly available, but these records 506 will typically include information about the specific PIN, and is the record that is updated when actions are taken on the rejection by the PAS.

Moving counter-clockwise from the prescription database 505 and associated records 506, the Patient (or Customer) Database 510 has records 511 for each customer. This data is where the information on the customer's healthcare plan and potential payers is, as well as other relevant information such as allergies, age, contact information, etc. Though this information is not a medical record (the pharmacy likely does not have access to the patient's medical records), it may include known medical conditions reported by the patient or by the prescribing physician that are relevant to possible prescriptions or treatments. As seen below, this information may be used to redirect to another payer, to screen for Medicare eligibility, to consider alternative fills, etc. It is also updated by the PAS when new information is obtained. Though shown as a separate record, the customer Rx history record 512 would also be a component of the patient database 510. This record provides information about the specific medications that the customer is on, or the prescription information relative specifically to that customer.

The insurance plans database 520 on FIG. 5 corresponds to the plan info record 521 on FIG. 5A. This database will have information known to the PAS about each specific payer, and the plans offered by that payer. Thus, the payer and plan may be identified within the customer record, but what the details are of that plan as relevant to filling prescriptions can be found in the plans database. Despite this name, the Insurance plans database would have information on all potential payers, including pharmacy benefits organizations, etc. The database may have specific information on a particular plan being billed, such as, so that the PAS knows the amount of the co-pay, or can anticipate even before submission what should be covered and what should not. In these cases, the PAS may be used by system administrators to regulate and ensure that payers are offering the pricing and coverage that has been negotiated through the pharmacy, if applicable. Even where specific plan information is not available, this is where historical information on the payer relating to past rejections and/or peculiarities with respect to rejection coding and resolution would be housed.

The Rules History Database 530 does not have a corresponding record on FIG. 5A, but would hold data relating to particular logic rules, such as when they were effective, when they were not, when to apply them, etc. Meanwhile, the store info record 599 of FIG. 5A does not correspond to a database on FIG. 5, but that information would be within the PAS database. Specifically, it would have administrator level details about the various stores within the system such as contact information, and preferences of those stores as to what and when to automate, etc. Those preferences can be set through store computer 190 by the pharmacist.

Rejection History Database 540 has information about particular types of rejections, and provides another means for cross-referencing information from past rejections. Not to be confused with the prescription database that is organized by specific PIN, the rejection database is organized around rejection type, or message information within a rejection, so as to allow the PAS to determine potential resolutions by looking at how similar rejections were handled in the past. Each rejection data record 541 would contain information about rejections searchable by reject code or messaging. Finally, third party database 182, as discussed above, may hold information about particular drugs, particular providers, etc., and could be stored in records such as Drug NDC record 546. Though this information could be retained in the PAS database, it is preferably obtained from a source that is frequently updated and more likely accurate, such as a server or database maintained by the FDA, etc.

Figure 6:
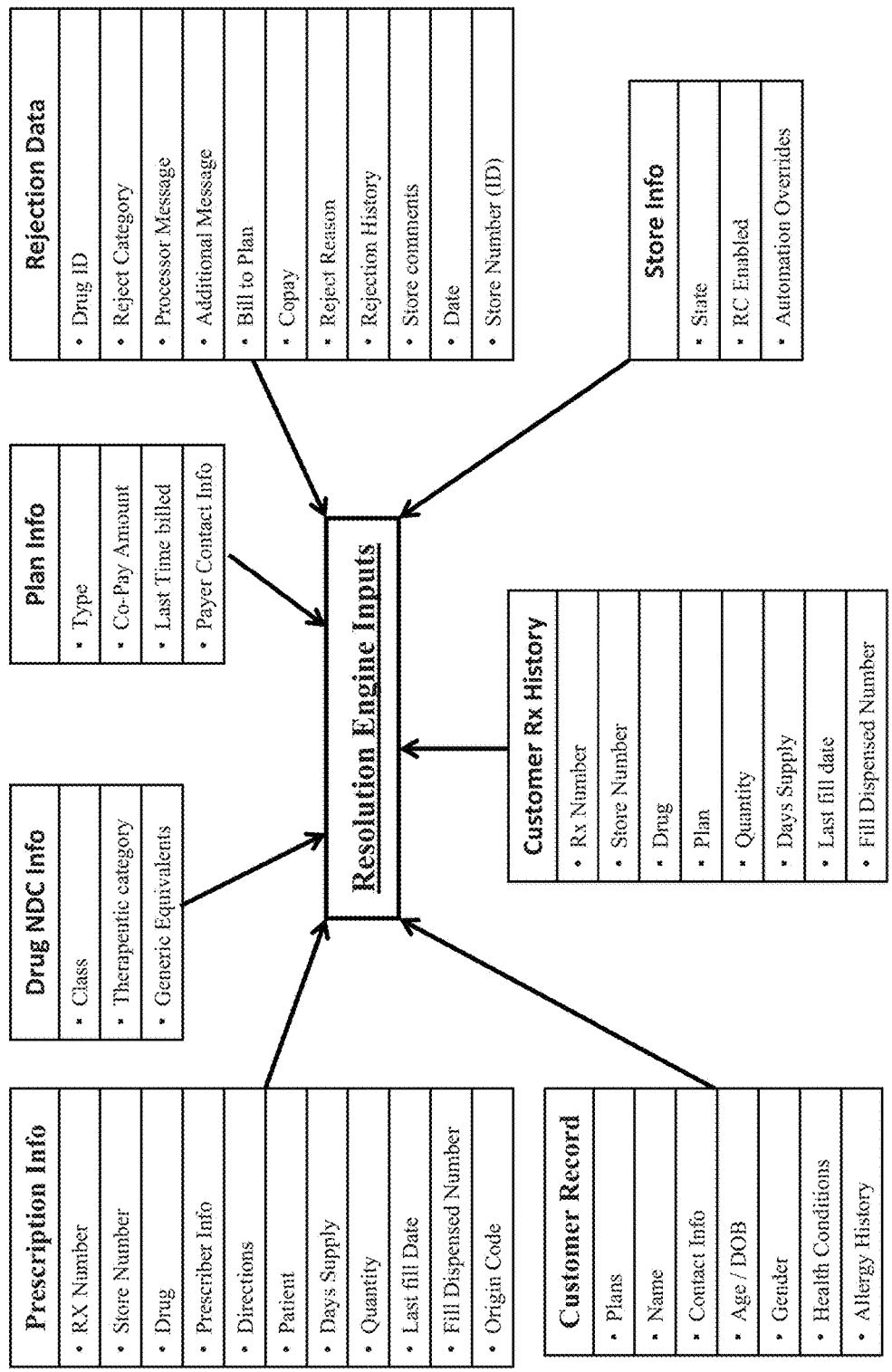
FIG. 6 is a data map showing information available to the resolution engine as inputs to resolve rejected prescriptions, in accordance with a particular embodiment.
Figure 6A:
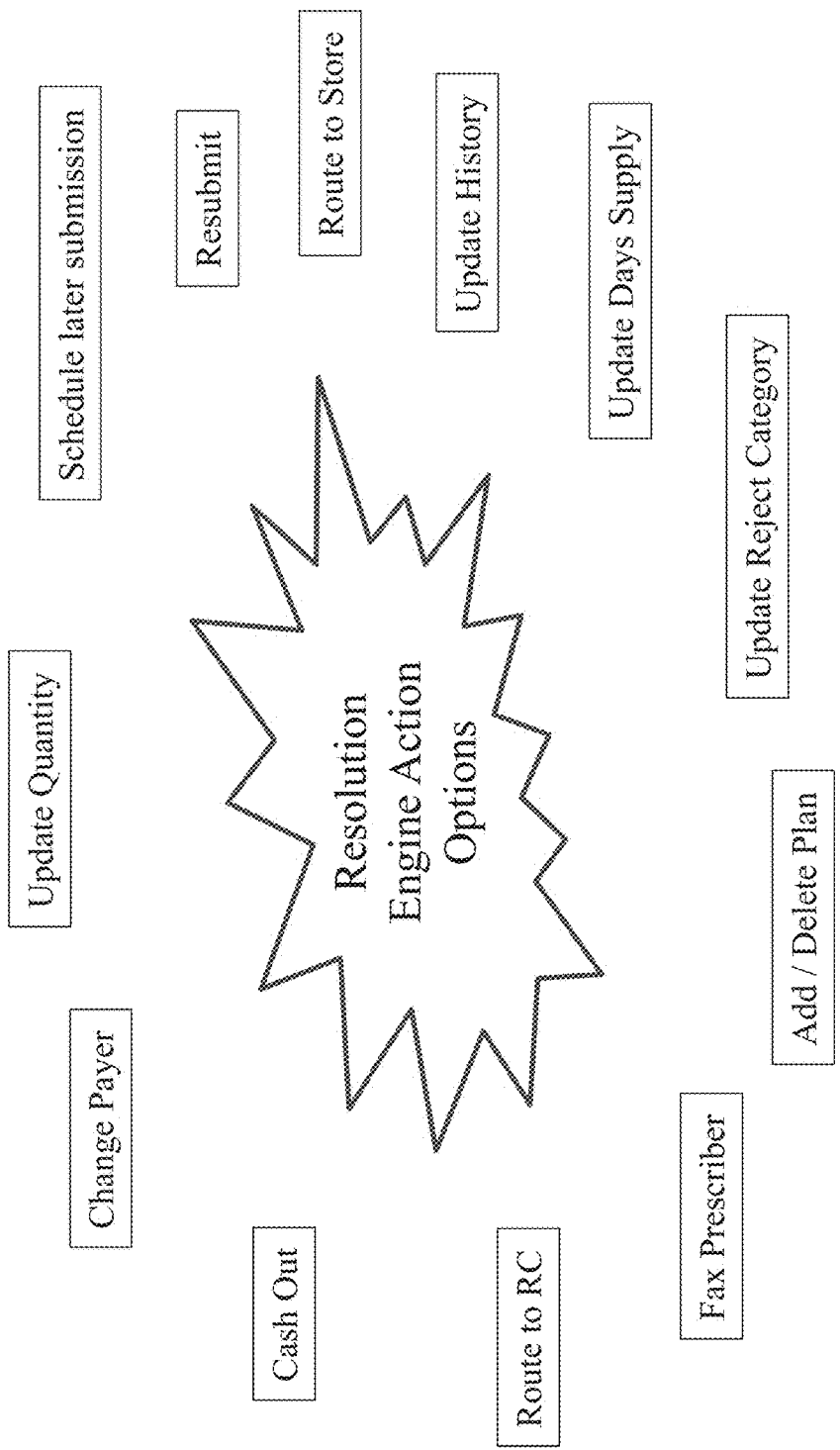
FIG. 6A is an activity map showing activity options or output modules that the resolution engine can choose from based on the particulars of the prescription rejection in accordance with a particular embodiment.

Just as FIGS. 5 and 5A demonstrate some of the inputs available to the Resolution Engine, FIG. 6 illustrates some of its potential outputs, or the activities that it is able to perform in an automated fashion. Each of these activities involve sub-routines, some of which are detailed more fully below. Deciding which sub-routine to execute (which action to take) is a factor of the logical analysis performed by the Resolution Engine based on all of the information (historical, empirical, and otherwise) available to it. Several of the action steps have already been mentioned and need no particular analysis, such as, for example, "Route to Store,"

"Route to RC" (resolution center), or "cash out," which is a term used to request full billing from the customer when no payer authorizes the prescription. But other actions involve sub-routines that are discussed in association with specific flowcharts in FIGS. 6-16, each of which divulge activity performed by the Resolution Engine 320. Thus, though there may be some overlap, the processes of FIGS. 6-16 are each symbolized by (and expansions of) step 230 of FIG. 4.

Figure 7:
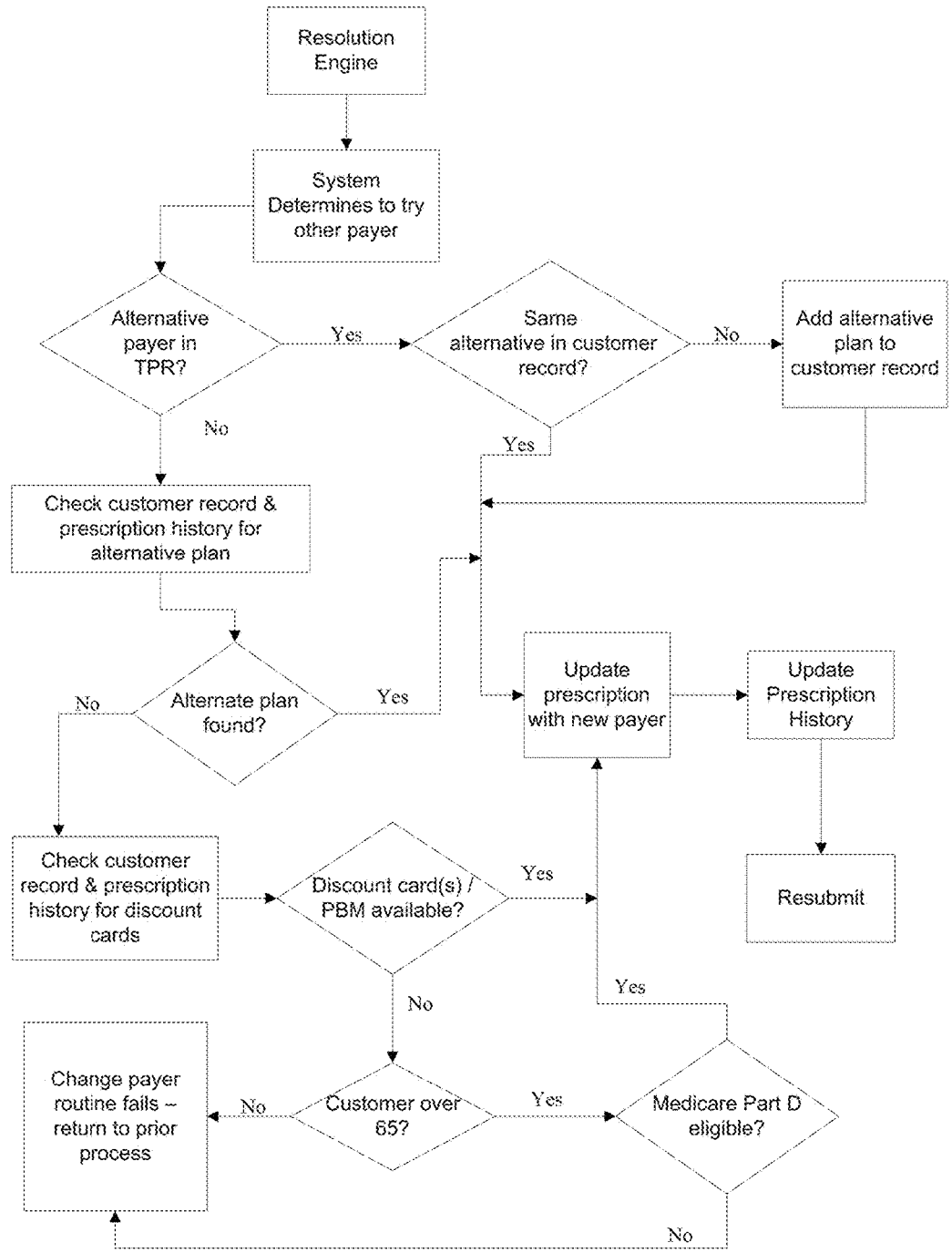
FIG. 7 is a flow chart showing the steps performed in a "change payer" module operated by the resolution engine in accordance with certain embodiments.
Figure 8:
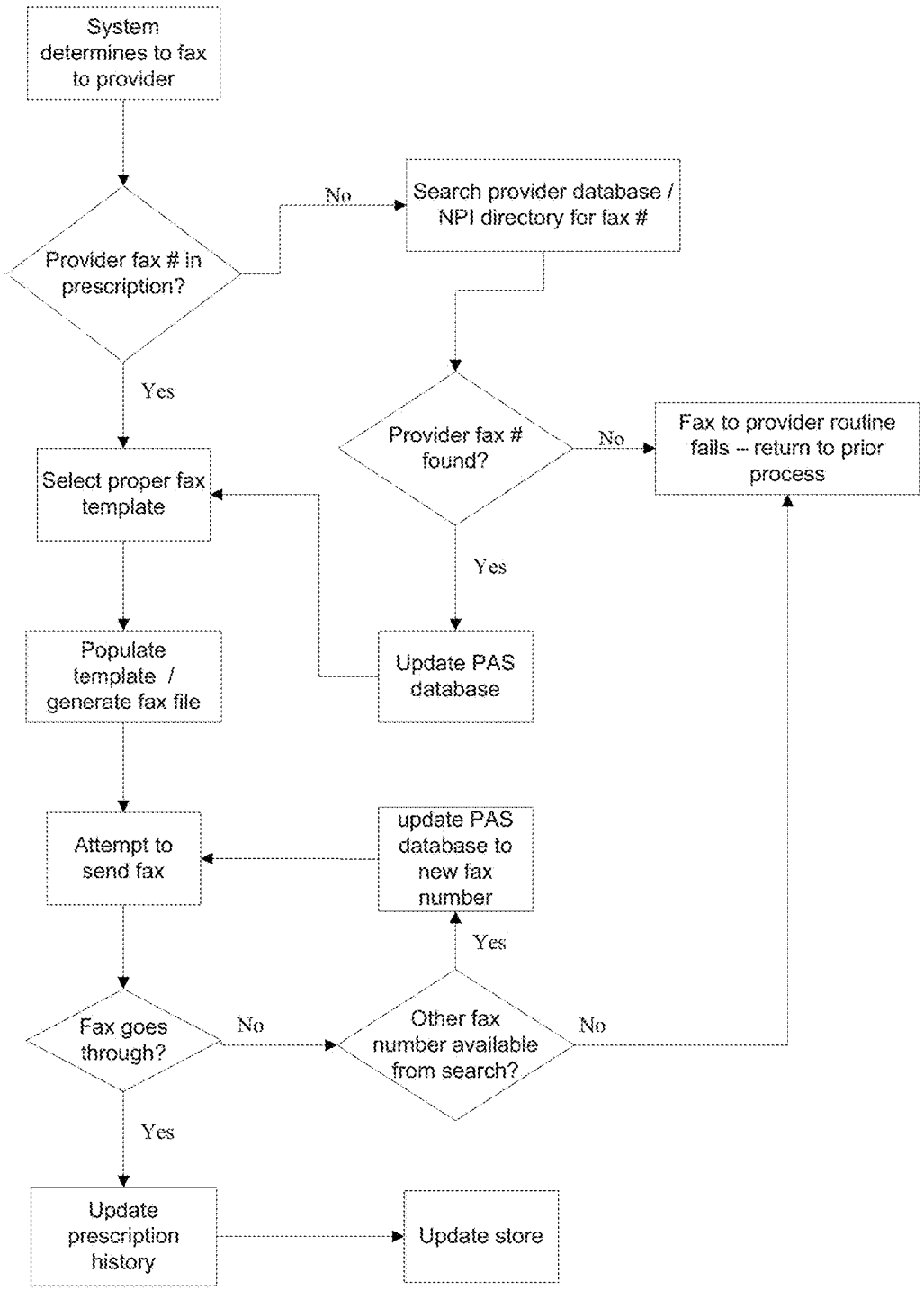
FIG. 8 is a flow chart showing the steps performed in a "fax to provider" module operated by the resolution engine in accordance with certain embodiments.
Figure 9:
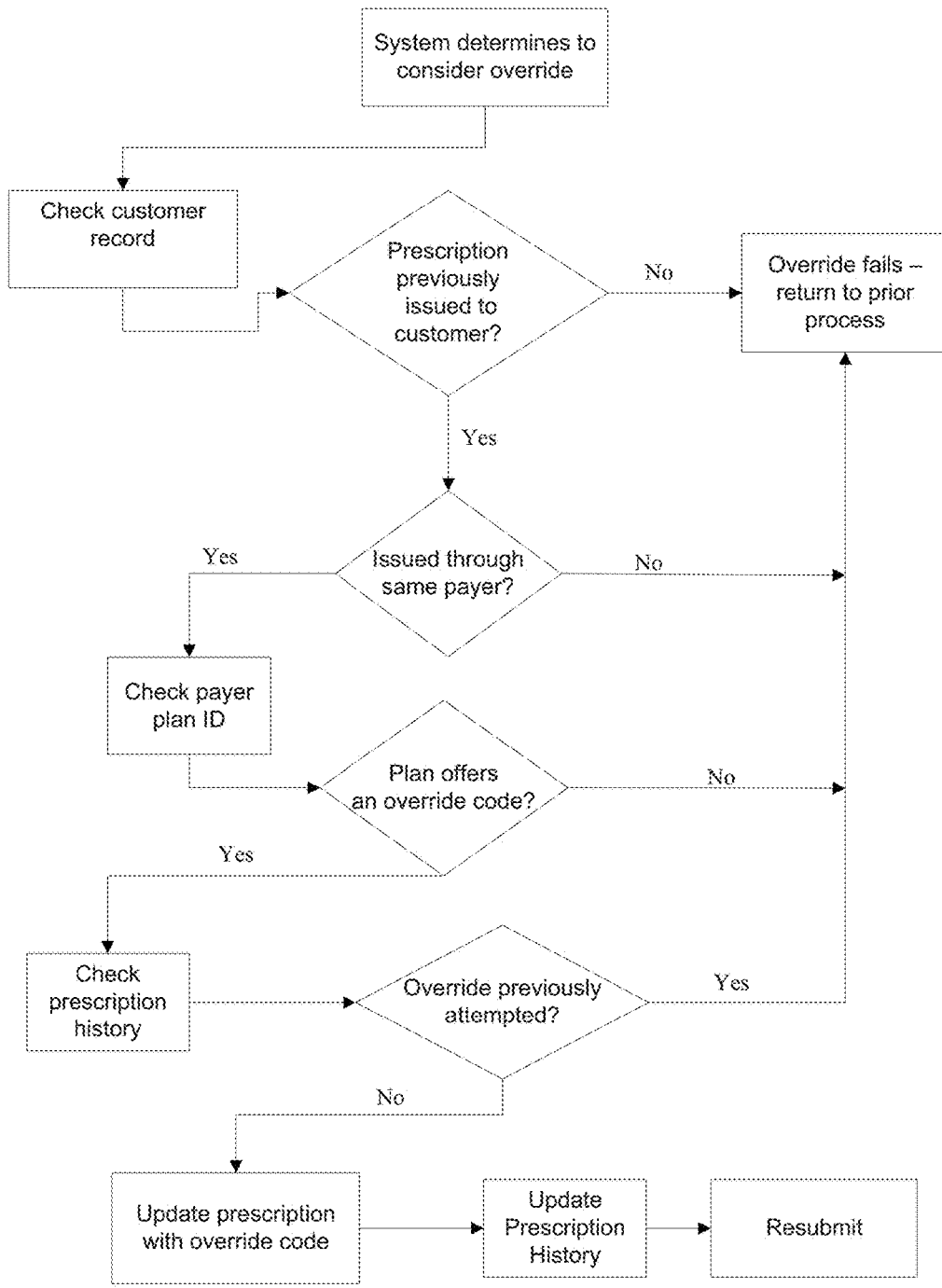
FIG. 9 is a flow chart showing the steps performed in an "override" module operated by the resolution engine in accordance with certain embodiments.

Moreover, some of the subroutines are actually modules or callable routines from within a specific category-based response subroutine of the Resolution Engine. For example, FIGS. 10-16 generally correspond to actions taken given a specific category assignment received from the Category Engine 315, whereas FIGS. 7-9 are callable routines that may be utilized as options within the actions taken for a given category, based on feedback or information found by the Resolution Engine 320 when taking those actions. For purposes of clarity, the exemplary callable routines are explored first. They are generally a Change Payer Routine (FIG. 7), a Fax to Prescriber Routine (FIG. 8), and an Override Routine (FIG. 9). These would correspond to potential "action options" on FIG. 6, though not nearly all are illustrated, and more could be added. Where a callable routine succeeds, the process through the Resolution Engine stops with resubmission and updating the prescription history. Where it fails, flow returns to the Resolution Engine to try other alternatives, or for further routing.

Turning to FIG. 7, a Change Payer routine is disclosed. This routine is called in a scenario where the Resolution Engine has determined that the payer to whom the prescription was previously routed is incorrect, or where attempts to get that payer to approve the prescription have not been successful. At step 700, the Resolution Engine decides to try another payer. In some cases, an alternate payer will be listed directly in the rejection messages. For example, the store might have a secondary insurance listed as primary for the patient, or otherwise may not have updated information. If the insurer has been informed of a primary insurance, such as when a person previously insured as single goes on a spouse's plan, etc., the payer may reject on the basis that it is no longer primary, and the primary payer should be billed. In this case, the rejection may provide information needed for the PAS to automatically change the payer and resubmit.

Any time the PAS learns new, relevant information, it is designed to update its own records. Thus, in the scenario described above (or in any other scenario where the rejection provides new payer information, the PAS verifies whether it has that information on file for the customer and, if not, it adds the alternative plan to the customer record at step 720. Adding or deleting plans on a customer record is itself a separate callable subroutine, however, it is not specifically laid out because the steps are fairly basic. Generally, it consists of updating fields within a customer record. Once this process is complete, the PAS updates the prescription to include the new payer information at step 730 and proceeds back to FIG. 3 flow (step 240) to resubmit the prescription.

More likely, there will not be any new information about payers in the rejection. In this case, the PAS will check the customer record for alternative insurance plans at step 705. If any alternative plans are found, it will proceed to step 730 to change to those plans and resubmit. If not insurance plans are found, it will then check for discount cards or other potential payment benefits at step 710. Once again, if found, the prescription will be updated and resubmitted with the benefit. Finally, if each of those options fail, the system will check the age of the patient to see if they may be eligible for Medicare, but not properly signed up within the system. If so, the PAS will attempt to submit through Medicare by again updating the prescription payer information. If all of these options fail, the overall Change Payer routine fails and, at step 750, flow returns to the prior process step that determined to try the Change Payer routine.

FIG. 8 discloses a Fax to Provider subroutine. This subroutine is used when the PAS Resolution Engine determines that some information missing from the prescription (or incorrect in the prescription) must be acquired from the provider. In the prior art, this would necessitate a manual determination followed by an exchange of phone calls trying to obtain the proper information. However, the PAS has the ability to auto-generate documents and send them electronically via facsimile transmission to the provider so that the provider can respond and resolve the issue without playing phone tag and without involving pharmacy personnel. Essentially, the PAS pushes the provider personnel to make the correction to the script, and the provider resubmits the prescription (with the correct information) in the same manner as they did before.

The PAS is able to generate documents by choosing from pre-designated templates and filling in information out of records stored within the PAS database and, as appropriate, out of the prescription database. For example, the document may have a specific header that populates the address and phone number of the pharmacy through which the prescription is issuing. Turning to FIG. 8, at step 800, a decision is made by the Resolution Engine that information is required from the provider, and to attempt the Fax to Provider routine. The first challenge is to find the fax number for the provider. This is ideally in the prescription data associated with the PIN itself. Alternatively, the first place to look is in the PAS database under the provider record. If a fax has previously been sent to that provider, the number should be there.

If not, the PAS may search for it in other places. As shown at step 820, the PAS may search the Health and Human Services NPI (National Provider Identifier) database, which is maintained by the Centers for Medicare and Medicaid Services, and is updated daily. Other options not listed at step 820, but also available, would be to check the Drug Enforcement Agency (DEA) database for the DEA number associated with the provider. A DEA number is a number assigned to a health care provider by the DEA allowing them to write prescriptions. It is often used by the industry as a general "prescriber number" that is a unique identifier for anyone who can prescribe medication. The PAS could also check within the patient record to see if information about their care providers (and particularly the provider in question) is present.

If a fax number can be found for the provider, the PAS updates the PAS database information relating to the provider (e.g., a provider record) so as to avoid the need to search next time (step 825) and proceeds to step 805. At step 805, a proper fax template is selected. The fax template will depend on what information it is that is deemed to be missing or incorrect in the prescription, as determined by previous steps of the Resolution Engine. These templates will be created in advance by system administrators and populated into the PAS database for use by the PAS. They have fields that correspond with information to be filled in from the rejection or other sources. The PAS populates the template at step 810 and attempts to send the automatically generated document via facscimile at step 815. This is facilitated by nature of the central PAS server 162 being equipped with connection to a phone line or standard fax machine.

If the fax goes through to the fax number, the routine has succeeded. If not, other numbers are searched for in the same manner as above. After a few attempts at sending the fax, the system will determine that the fax number is not good, and will update the appropriate records within the PAS database at step 830. Finally, if no numbers can be found that work, the Fax to Provider routine will have failed and at step 850, flow will be returned back to the prior routine that determined to call the Fax to Provider routine.

In success cases where the fax goes through, the process does not follow its normal steps of resubmission because either the provider will resubmit or the provider will provide information to the store for resubmission. Accordingly, there is no further action for the PAS to take, and there may be a waiting period while the provider takes action on the fax. Thus, the PAS takes its normal step of updating the prescription history at step 235 and then proceeds to update the store at step 875. In this manner, the store will be aware that it is waiting on the provider, and not on the PAS or the resolution center to take action. The step of updating the store may be in the form of sending a text or email message with details of the actions taken, and/or it may include sending a copy of the fax to the store so that it has a copy of what the provider has received. If no action is taken by the provider after a reasonable time, then the store can contact the provider and reference the fax and the time it was sent, in order to get priority attention to the matter.

FIG. 9 illustrates an override routine. Some payers allow for an override of their rejection in certain situations. For example, a person may not be ready for a refill for another week, but they are leaving on vacation and need to obtain the refill in advance. In other cases, a plan might require a generic equivalent, but the provider has specified that no substitutes are to be allowed. In still other cases, there may need to be some special signoff to administer a drug to someone of a particular age. Where the proper information is present within the PAS (such as records of approval, etc.) to attempt an override, one may be submitted automatically if certain criterion are met.

At step 900, the Resolution Engine determines to attempt an override of a payer's rejection. Though not always the case, where a prescription has never been issued to a patient before, it is less likely that an override is proper. This would eliminate the scenario, for example, where someone simply wants an early refill, or a different dosage format, etc. Thus, the routine as set up in FIG. 9 will not automate an override for new prescriptions, preferring that these be entered manually. However, this safety check associated with step 905 is not necessary and may be removed. As it is, at step 905, the system check's the customer record to verify that the prescription is a renewal and not an original. If so, it passes on the override path. If not, the override routine fails at step 950 and passes back to the routine from which it was called.

If it continues along, the system then checks to see if the prior prescription was through the same payer. The theory here is that a payer will not likely approve what, to them, is an override on a new prescription. If it is with the same payer, the PAS checks the plan record in the Prescriber database and determines whether the plan offers an override code. Some plans do not, in which case this routine fails. Finally, at step 915, the PAS checks to determine whether, despite the prescription being previously issued to the customer through this payer, and the payer having an override code, the code has been attempted on the prescription in the past for the customer and failed. If so, it will not be attempted again. However, if it has not been tried, the PAS will update the prescription with the override code at step 920, updates the prescription history, and then resubmits the prescription at step 240. The system includes these various checks against pursuing an override code, in part, to prevent objections from the payers, but also to avoid potential issues with improper use of them.

Again, FIGS. 10 through 16 each reflect action paths taken by the PAS in the case of particular categorization of the rejection received from the Category Engine 315. There are more potential categories than the seven illustrated, but these are the primary ones that have been adapted for handling by the Resolution Engine 320. The first category, which is associated with FIG. 10, relates to a perceived or anticipated mistake with the days of supply of the medication within the prescription. FDA guidelines, payer guidelines, or other rules may restrict the number of days of supply that a person can have of a particular medication. This may be for a variety of reasons. For example, the effectiveness of the medication may fade or expire over time, or it may decay or mold. In some cases, the medication may be a narcotic in which case there may be concerns with possible addiction or misuse. In other cases, side effects may require checkups in between prescription fills to ensure that the medication is working properly and not causing harm. In any event, prescriptions are often rejected when the payer calculates or determines that the amount of the medication being prescribed is too much such that the days supply would be exceeded.

How the Categorization Engine reaches the conclusion to categorize as a "days supply" error may be so simple as that being the reject code listed in the rejection. However, as discussed above, reject codes are not always correct, and the Categorization Engine may have categorized as a days supply error based on its own determination. For example, the PAS would have access (through the PAS database, the payor database/plans records, or perhaps a government database) to information about the standard allowable days supply for a particular medication being prescribed. The prescription would also have information about dosage, quantity requested, and length of duration of use, etc. This information, along with the date of the prescription, could be used by the PAS to determine a problem with the days supply. Thus, even if nothing in the rejection suggests or indicates a days supply error, this is a standard check that the Categorization Engine can run. Where the check produces a likely days supply issue, the categorization feeds into the flow of FIG. 10 at step 1000.

In order for the Resolution Engine to potentially resolve a days supply issue, it first must determine the maximum days supply for the medicine, that is, the number of days of supply of the medication that a patient is allowed to have on hand. This amount is typically set by the provider, and is a component of the prescription, but that is not always the case. Also, the prescriber may identify a max days supply that is greater than the amount of the medication allowed by the government or some regulating body, or by the payer. In the case of some specialty drugs (for example, "C2" drugs), the state will likely have a limit on the supply that can be prescribed.

Even if the supply is not government controlled, there may be an arbitrary amount of supply set by the payer. For example, the plan may indicate that a particular drug may only be authorized in 30 day increments. If the payer has set such a max days supply, ideally it will include this in the processor message or additional message of the rejection. ("TPR" in the decision box of FIG. 10 and other figures of the flowcharts stands for "third party rejection." In other words, is the max days supply listed in the processor message or additional message?) If not, at step 1060, the Resolution Engine searches for a Max Days Supply associated with the medicine.

The first place to look would be in the plan database to see if historical information is available from the payer to determine what it considers the max days supply. After that, the information could also be found in past resolutions specific to the customer (who perhaps has been prescribed the medicine before) or the prescription database (from others who have). Failing this, a governmental database may have information if the max days supply is set by the government.

The PAS is able to determine information from third party databases or other places about a particular medication by using its National Drug Code (NDC) or its Generic Product Identifier (GPI). All drug products are identified and reported using a unique, three-segment number, called the National Drug Code (NDC), which serves as a universal product identifier for drugs. The FDA publishes the listed NDC numbers, and the information submitted as part of the listing information in the NDC Directory which is updated daily. The GPI provides even more information. The GPI is a 14-character hierarchical classification system that identifies drugs down to manufacturer and pill size. The code consists of seven subsets, each providing increasingly more specific information about a drug available with a prescription in the United States. The first 10 digits of the GPI define the therapeutic class code and the last 4 digits define route, dosage or strength. For example GPI 58200060100105 is for the drug Nortriptyline HCL cap 10 mg (an antidepressant) and can be further classified as follows:

| 58 | Drug group | Antidepressants |
|---|---|---|
| 58-20 | Drug class | Tricyclic agents |
| 58-20-00 | Drug sub-class | |
| 58-20-00-60 | Drug name | Nortiptyline |
| 58-20-00-60-10 | Drug name extension | Hydochloride |
| 58-20-00-60-10-01 | Dosage form | 10 mg |

Figure 10:
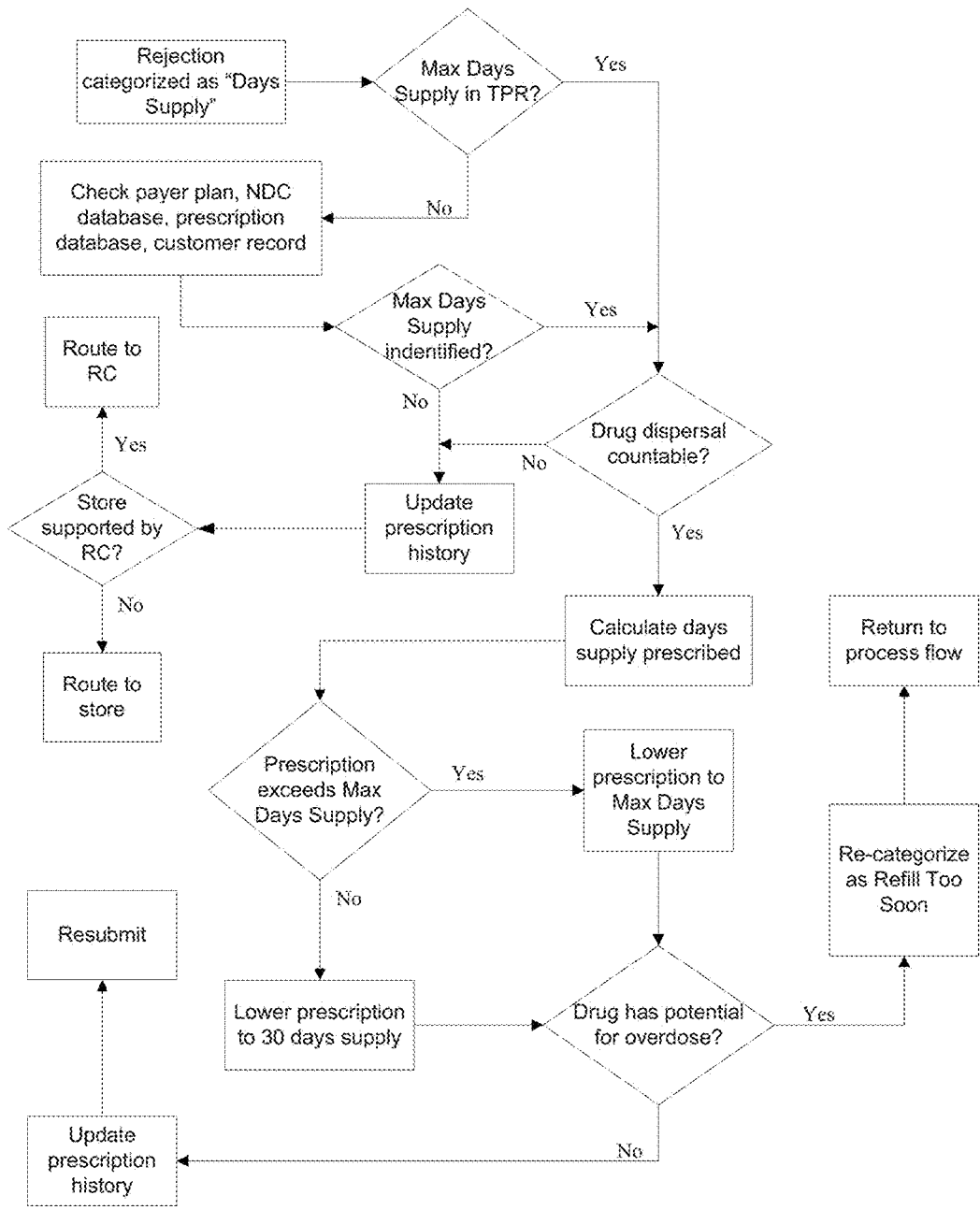
FIG. 10 is a flow chart showing steps performed by the resolution engine when a rejection is categorized as a mistake with the days of supply, in accordance with certain embodiments.

If the Resolution Engine is able to determine a max days supply, or at least to infer an educated guess as to what the max days supply likely is, then the subroutine of FIG. 10 can proceed to resolution. If not, the subroutine has failed to resolve the issue. The work performed is appended to the prescription history at step 235, and the Resolution Engine determines where to send the rejection. Because there is no basis for re-categorization, the rejection must either go to the resolution center at step 251 for manual resolution, or back to the store at step 250. In either case, the store or the resolution center will have the benefit of the prescription history to see what has occurred with the rejection up to that point.

If there is a max days supply identified, generally there will be a dispersible count for the medication. For example, there will be a set number of pills within a container, or a specific volume of fluid within a bottle. From this, given a prescription to take a certain number of pills or swallow a certain number of milliliters along a specific schedule, a specific day as to when the medication will run out can be determined. However, some prescriptions may be for items the supply of which cannot be specifically determined, such as, for example, topical ointments. If a "max days supply" is provided with such a medication, it indicates that there is an error in the rejection or prescription at a level that cannot be fixed by the Resolution Engine, and the path flows to the resolution center or back to the store after the issue is documented in the prescription history.

If the drug dispersal is countable, then the Resolution Engine calculates the days supply prescribed at step 1010. For example, if the prescription provides 90 pills at 2 pills per day, there is a 45 day supply. If this exceeds the max days supply, then the Resolution Engine updates the prescription at step 1020 to only issue the max days supply amount. In this example, if the max days is 40, it would be 80 pills. As a default, in the FIG. 10 example, the Resolution Engine lowers the fill to a 30 day supply at step 1030 if the max days supply is not exceeded. Most plans will accept a 30 day supply, and few medications are restricted to less than that. Accordingly, this is usually a default way to overcome a rejection based on days supply. While it may be inconvenient for the customer to have to renew the prescription in a shorter window than what was prescribed, it is generally preferred over the customer paying out of pocket because of the payer's rejection.

As shown, as a final check for this routine, the Resolution Engine checks to see if it can determine if the medication prescribed is of a narcotic type, a type that may have street value, or otherwise has a potential to be misused. This may involve checking the drug across a list stored in the PAS. If the drug is on the list, as a precaution, the Resolution Engine also runs the "refill too soon" subroutine. Having lowered the days supply, it may clear the rejection if resubmitted. But the patient still could end up with too much medication if they are submitting for a refill earlier than they should based on their prior fill. In many cases, this is not a concern. At worst, it may come back from the payer with a new rejection that will get categorized as "refill too soon." Thus, the history is updated at step 235 and the prescription is resubmitted with the shorter days supply at step 240. However, if it is a specialty drug, the PAS automatically re-categorizes at step 1040 and proceeds to the "refill too soon" routine (by returning to process flow at step 1050.

If the categorization is "refill too soon" (whether by way of re-categorization by the Resolution Engine, or by initial categorization of a rejection from the Category Engine), this typically means that the prescription has been submitted in advance of when the patient should need a refill. Sometimes there are legitimate reasons for submitting a refill early, such as when a patient is going on vacation or an extended work trip, etc. In that case, an override may be appropriate. When a rejection is delivered with the category of "refill too soon" to the Resolution Engine 320 at step 1100, the Engine will check for comments in the prescription history that would indicate a reason for early resubmission. If found, in some embodiments, the Resolution Engine my call the Override subroutine discussed above. Alternatively, as shown on FIG. 11, the Engine will either route the rejection to the store (step 250) or the resolution center (step 251) if the latter is supported. In most cases, this form of override will require human authorization.

Barring any information or comments that would suggest the premature refill was purposeful, the Resolution Engine will search for a refill date provided within the messages of the rejection. If the refill date is provided, the Engine will determine how many days until the next refill at step 1130. If the refill date is not provided, the Engine will attempt to determine it from available information. Typically this will have to come from the patient records. Assuming this is for a refill, the customer record should identify the last date the prescription was filled, and the days supply. From this, the refill date can be determined at step 1120, and then the days until that refill date at step 1130. If this information is not available, the routine fails and the Engine routes to the store or resolution center for next steps.

Figure 11:
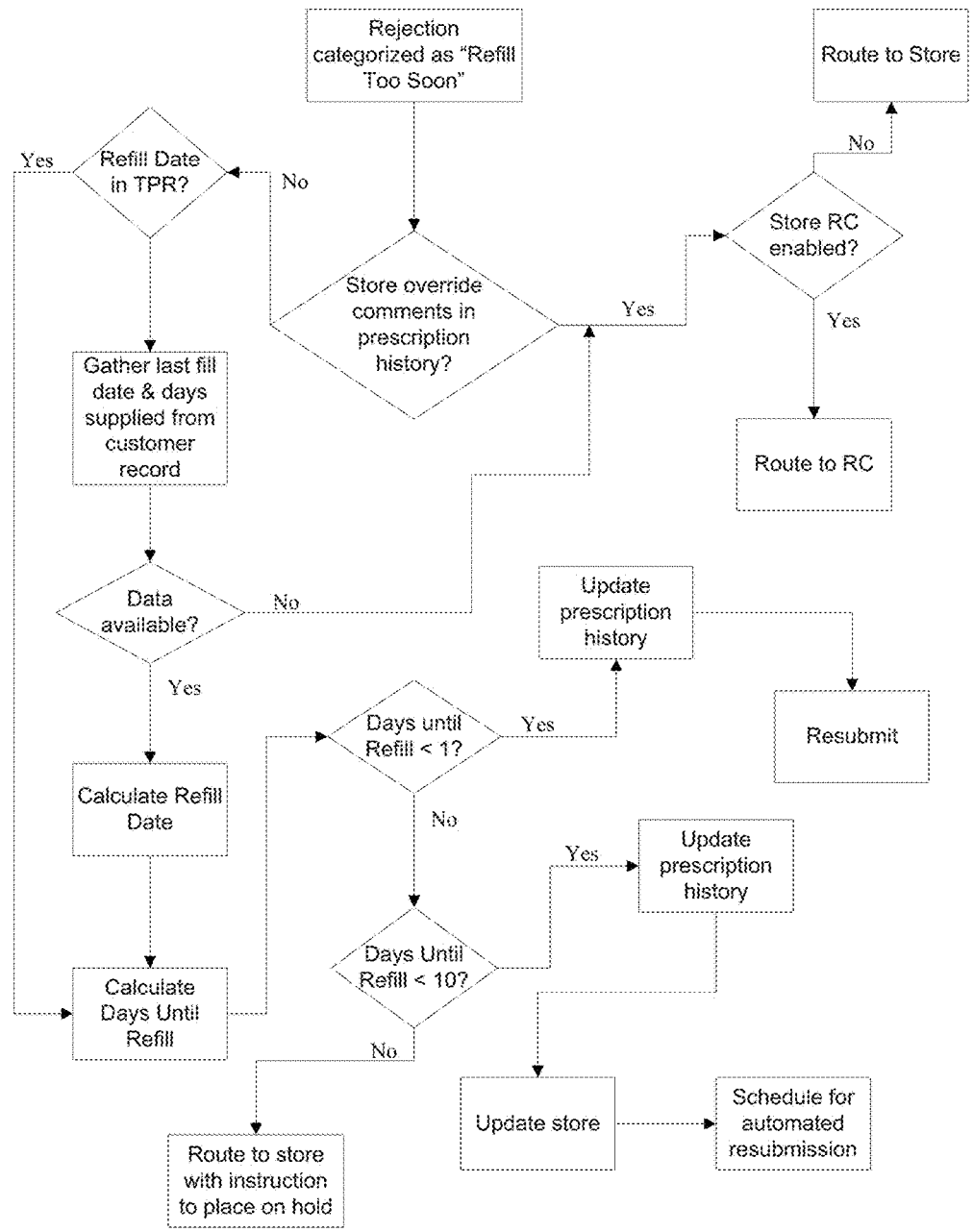
FIG. 11 is a flow chart showing steps performed by the resolution engine when a rejection is categorized as a mistake with the refill date being too soon, in accordance with certain embodiments.

If the Resolution Engine determines that the refill date is now, then there is no issue with early submission. The PAS updates the prescription history to reflect this at step 235 and resubmits the prescription for approval at step 240. If not, the Resolution Engine makes a determination to either hold the prescription and set an automated resubmission date closer to the refill date (at step 1140), or the prescription is returned to the store with instruction to place on hold (step 1150). This determination is based on the amount of time until the refill date. In the example of FIG. 11, the amount of time is set to ten days. Thus, if the prescription was resubmitted far too early, the system puts the onus on the store (and ultimately the customer) to resubmit closer to the renewal date. However, the refill date is close, the system will handle the resubmission and "bank" the prescription until the appropriate time. In the latter case, the prescription history is updated (step 235) and a message is sent to the store at step 276 advising it (and, ultimately, the client) of when the prescription will be resubmitted.

Figure 12:
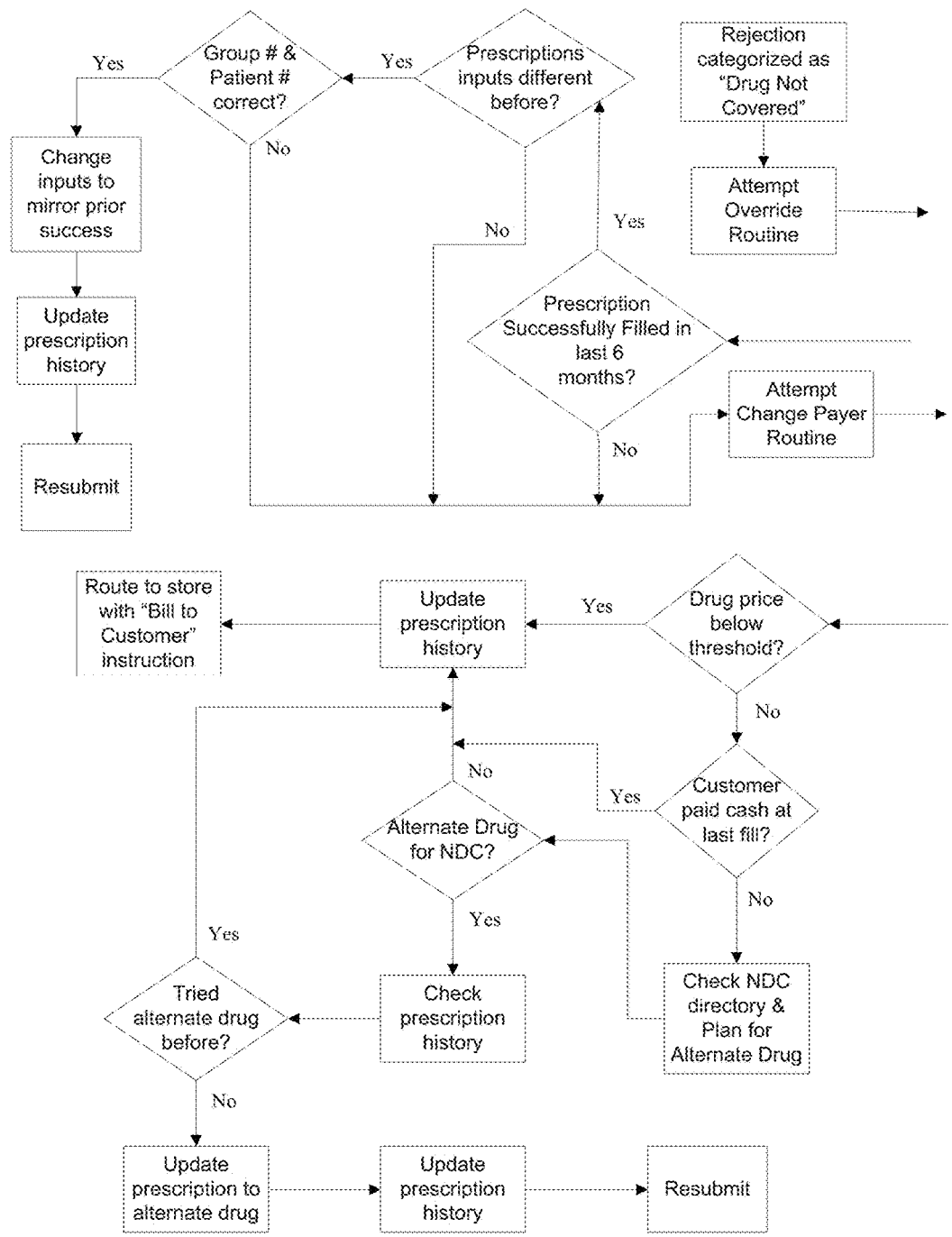
FIG. 12 is a flow chart showing steps performed by the resolution engine when a rejection is categorized as a mistake with the drug type being prescribed, in accordance with certain embodiments.

FIG. 12 illustrates steps taken by the Resolution Engine 320 when the categorization is "drug not covered." This is a PAS system indication that the Category Engine 315 has interpreted the rejection to result from the fact that the payer will not cover the medication prescribed. There may be many reasons for this. In some cases, the medication is simply outside of the plan or contract, and the payer is not obligated to cover it. In other cases, the payer may believe that a generic equivalent is available, and requires the prescription to be changed to the generic equivalent. In some embodiments, the PAS is enabled to make this change, as discussed below. However, there may be state rules against a pharmacy changing (even to a recognized generic) without the prescriber's agreement. In other cases, the prescriber may have indicated in the prescription that no generic equivalents are to be substituted. This is typically done with the comment "dispense as written," indicating no alterations are allowed. The PAS is able to check for such comments in the prescription and follow them by routing the prescription to the store and not altering it. But if there are no such comments and a generic equivalent is available, the PAS may alter and resubmit the prescription if such capability is enabled by the system administrators. This is a scenario that could be enabled for one store, but not another, for example, located in a state where this would be prohibited.

In other cases, a payer may reject a medication due to the strength or some other aspect about its dosage instead of the type of medication itself. Again, if the prescriber includes the "dispense as written" language, it should not be changed. Otherwise, the form of the medication (for example, from liquid to pill, or from an instruction to take 2×250 mg pills to an instruction to take 1×500 mg pill) can also be changed by the store, or by the PAS if so enabled by the system administrator. In some configurations, the PAS can simply recommend the change to the store, such as via comments in the prescription history, but not make the change and resubmit on its own.

While there are several methods disclosed to address a "drug not covered" scenario, FIG. 12 allows for a reasonable level of automation, with appropriate checks built in. Though the PAS is ultimately authorized to change to an alternate drug or change the delivery, other options are exhausted first. Here, the rejection arrives at the Resolution Engine 320 as a "drug not covered" categorization at step 1200. The system first calls the Override subroutine (see above discussion in association with FIG. 9). This will handle scenarios where a recurring prescription is receiving a similar rejection, and an override code is available. If this works, the flow ends and resubmission is handled through the Override subroutine. If not, the Override subroutine will return to the "drug not covered" routine of FIG. 12, and the PAS will look into the patient history to see if a prescription for the same medication has been approved in the past. If so, and the system detects differences between how the prescription was previously submitted, it will change to the former inputs at step 1210, update the notes on the prescription and resubmit at step 240. This will correct spelling or data entry errors and other common issues.

If there was no prior prescription, or if there was but it was entered the same way, or if there is now a new payer involved, the Resolution Engine will next attempt the Change Payer subroutine (see above discussion relating to FIG. 7). Again, if this succeeds, resubmission will occur without return to FIG. 12. However, if changing payer is unsuccessful, flow will return and the Resolution Engine will check the price of the medication. If it below some pre-designated threshold (say $10), there is no sense in searching for a generic equivalent and most likely the patient will simply accept the charges in full. In this case, the history is updated (step 235) and the rejection is routed back to the store with a "bill to customer" instruction (step 290). The actual threshold amount can vary from store to store, and is a variable that the stores can set based on their own customer satisfaction experiences.

Where the price is not below the threshold, the system will check the customer record to see if the customer paid cash for the same medication in the recent past (despite the high price). If so, this indicates to the PAS that the customer has accepted the fact that no payers will assist with the cost, and the PAS again forwards to the store at step 290 for full payment by the customer. Only if the cost is above the threshold and there is no history suggesting customer payment in the past will the Resolution Engine search for an alternate medication (generic equivalent, etc.).

The NDC directory typically will list the generic equivalents for a medication (if any). In some cases, the rejection from the plan will specifically identify the generic equivalents that it will accept in place of the name brand medication. The system checks for this information at step 1220. If it finds no alternatives, despite the cost, the Resolution Engine has been unable to get approval by a payer and the rejection is returned to the store for full payment. Where an alternative medication is identified, the PAS checks the prescription history at step 1230 to see if the alternative medication has been attempted before. If so, this change will not likely succeed on the second pass where everything else remains unchanged, so the rejection is again returned to the store with a bill to customer annotation. If it has not been tried before, then the Resolution Engine modifies the prescription to change to the alternative medication at step 1240, updates the prescription history at step 235 and resubmits with the alternative medication at step 240.

Figure 13:
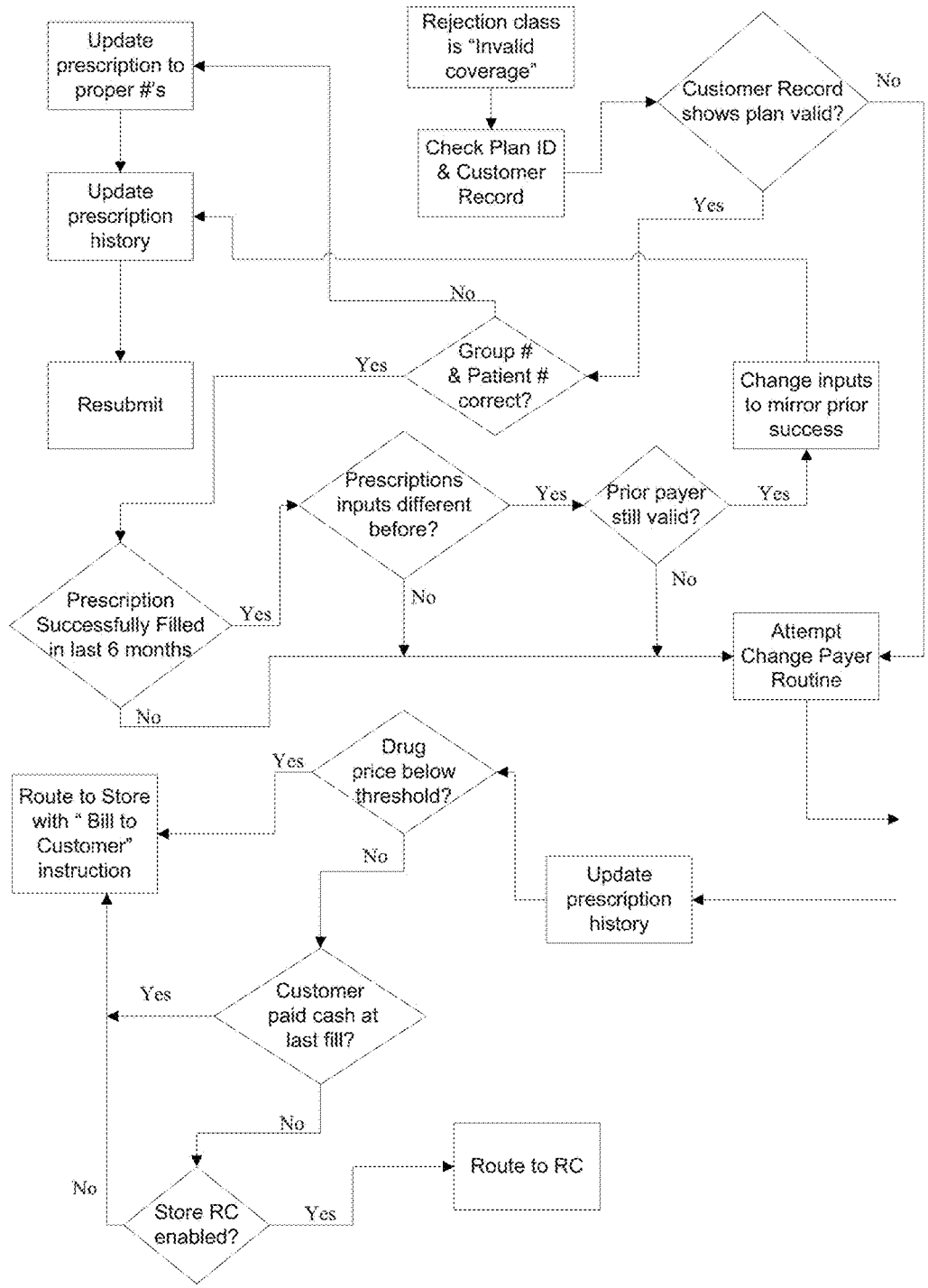
FIG. 13 is a flow chart showing steps performed by the resolution engine when a rejection is categorized as a mistake with the insurance coverage of the patient, in accordance with certain embodiments.

FIG. 13 provides an embodiment for a routine of the Resolution Engine where a rejection arrives at step 1300 with a category of "invalid coverage." This category usually indicates a mistake with the customer's plan information, namely that the person is not listed on the plan. For example, they may have changed insurance providers, they may have gone onto a spouse's plan, or they may not be listed on the plan submitted, etc. In accordance with the embodiment shown in FIG. 13, at step 1310, the Resolution Engine checks information on file within the customer database to determine if the plan submitted is in the customer file of the pharmacy. If not, the system launches the Change Payer subroutine at step 1307. If so, the Resolution Engine verifies whether the plan information (group number, member number, etc.) was properly input. If not, that information is updated at step 1320, the proper annotation is made to the prescription history, and the prescription is resubmitted at step 240.

Where the plan is on file and the information submitted was accurate, the system checks whether a prescription for the same medication was approved in the past six months. If so, and the payer used is still valid, the system changes the inputs to mirror what was previously approved at step 1330 and resubmits. Otherwise, it assumes that the information in the customer record is no longer correct, and launches the Change Payer subroutine. If the subroutine works, the prescription will be resubmitted within that subroutine. If not, flow will return at the bottom right of FIG. 13. This portion shows a slightly different variation of final resolution that FIG. 12. Here, the prescription history is updated at step 235 and then a determination is made on the price of the medication. If below the threshold, it is routed to the store for full payment by the customer at step 290. If not, a check to the customer history is made to see if they paid in full the last time. If not, then a check is made as to whether the store is supported by the resolution center. From there, the rejection will either be routed to the resolution center at step 251, or to the store with a suggestion to bill to the consumer at step 290.

Figure 14:
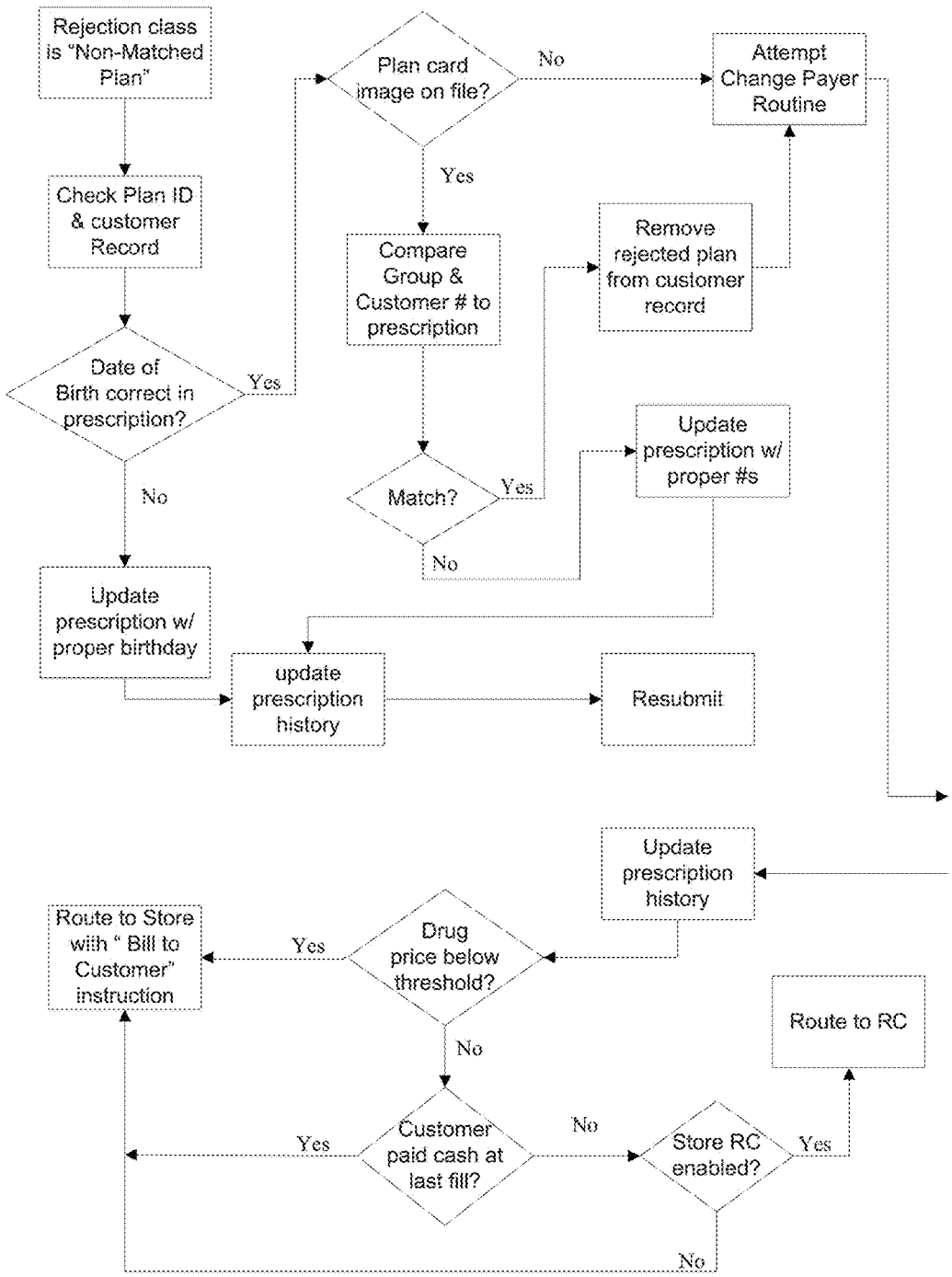
FIG. 14 is a flow chart showing steps performed by the resolution engine when a rejection is categorized as a mistake with the matching of the payer plan and the prescription, in accordance with certain embodiments.

FIG. 14 provides an embodiment for a routine of the Resolution Engine where a rejection arrives at step 1400 with a category of "non-matched plan." This category usually indicates a mistake with the customer's plan information, namely a mistake with the data submitted with the plan. While similar to "invalid plan," here the Category Engine 315 is not suggesting the person is not covered, but that some information submitted in association with the plan is inaccurate. At step 1410, the Resolution Engine checks the plan information on file with the customer. The first verification is that the date of birth for the patient matches. If not, the system corrects the prescription and resubmits with the proper date of birth.

If the birthday is correct, the system checks for a scan of the customer's insurance or other payer card on file in the customer database. It may be that, even if the information within the customer record matches the prescription information, they both may be wrong due to a data error entry. If a scan is find, the Resolution Engine checks the scanned image information against the information entered in the customer record at step 1430. If these do not match, the scanned images is deemed to be the correct information and the customer record information is updated by the system at step 1450. The prescription is likewise updated and then resubmitted. Where the scanned image exists and matches the information in the customer record, the assumption is that the plan is no longer valid for the customer. In this case, the plan is removed from the customer record at step 1440 and the Change Payer routine is called at step 1407. (This is also the default if no scan of a payer card is found.)

If the Change Payer routine is successful, the resubmission occurs from within the subroutine, and flow does not return to FIG. 14. However, if Change Payer fails, flow returns and the history is updated at step 235. From there, the steps followed mirror that of FIG. 13, e.g., routing is based on price of the medication and, if over the threshold, whether the store is supported by the resolution center.

Figure 15:
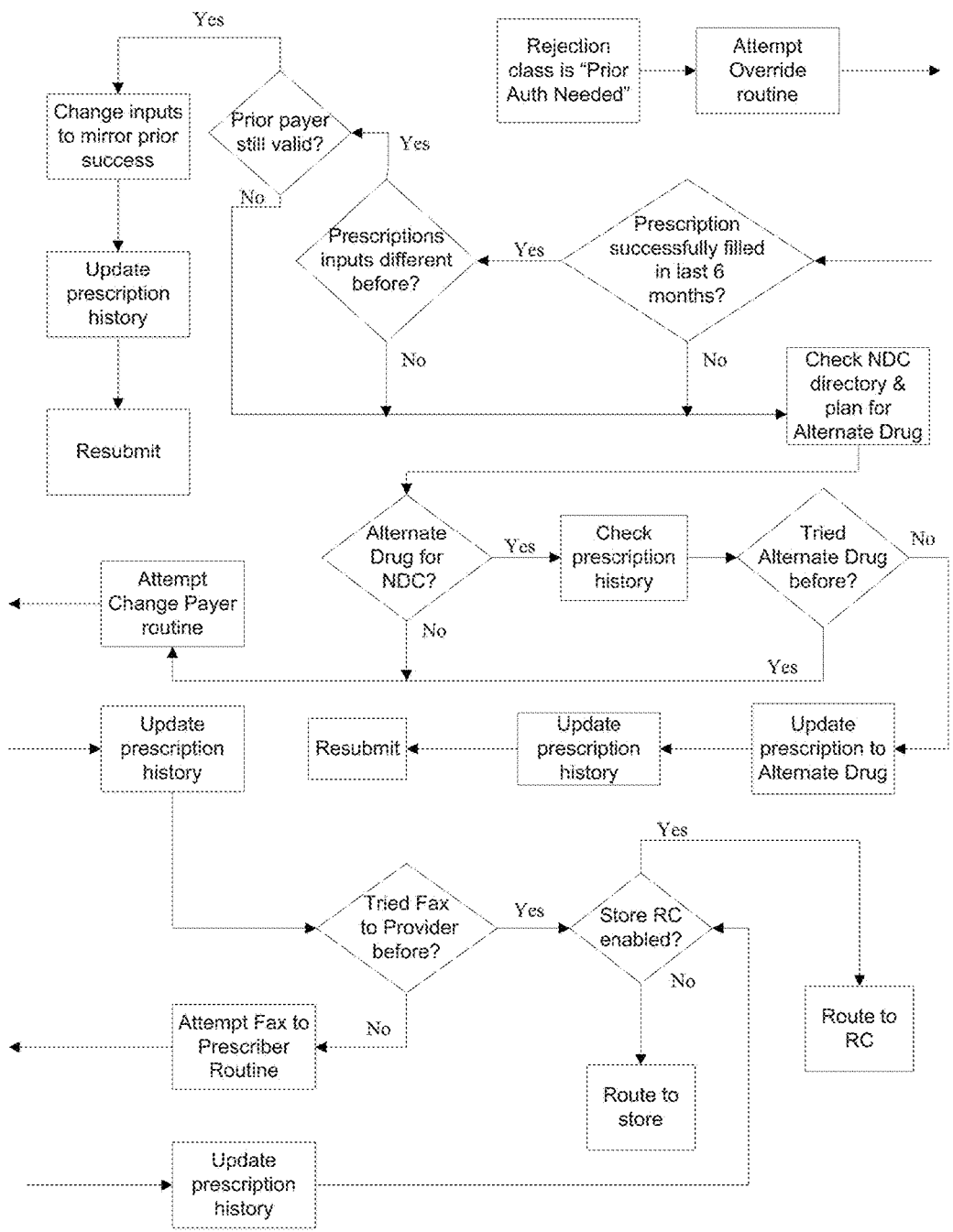
FIG. 15 is a flow chart showing steps performed by the resolution engine when a rejection is categorized as a mistake due to prior authorization for the medication prescribed being required, in accordance with certain embodiments.

FIG. 15 provides an embodiment for a routine of the Resolution Engine where a rejection arrives at step 1500 with a category of "prior authorization needed." This category usually indicates that the plan is requiring some form of authorization from the provider due to, for example, the type of medication or the age of the patient. Similar to the "drug not covered" routine of FIG. 12, the first step shown in FIG. 15 is to attempt the override subroutine at step 1510. If the override succeeds, resubmission will occur from there. If not, flow will return and the PAS will check the customer database to see if the prescription has been recently filled for the customer. If so, and the prescription inputs were different, and the payer used then is still valid, the PAS will revert to the prior prescription inputs at step 1520, update the prescription history at step 235 and resubmit the prescription at step 240. Otherwise, the Resolution Engine will search for an alternative (e.g., generic equivalent) medication within the plan information, the NDC database, or other historical information within the PAS database relating to the medication at step 1530.

The Resolution Engine resorts to looking for an alternate more directly in a prior authorization case than in a drug not covered case because the latter is typically easier to overcome or more likely to be a mistake. If an alternate is found, the system checks the prescription history at step 1540 to see if it has already been attempted on a previous pass through the PAS. If not, the Resolution Engine alters the prescription to identify the alternate medication at step 1550, updates the prescription history and resubmits the prescription. If the alternate has already been attempted, or if no alternate was found, the system attempts the change payer routine at step 1507 to see if the need for pre-authorization can be avoided through another payer. If this works, the prescription will be resubmitted from within that sub-routine. Otherwise, flow will return and the history will be updated at step 235. In this case, the Resolution Engine concedes that pre-authorization must be obtained and checks to see if an attempt to fax to provider has been tried before.

If fax to provider has not been attempted, this sub-routine will be called at step 1508. If successful, resolution is determined within that subroutine after the fax is successfully sent (which would correspond to a pre-defined template seeking pre-authorization for the prescription from the provider). If the sub-routine fails, for example, because the fax number for the provider within the PAS database is incorrect or no fax number is found, flow will return and the history will again be updated. From this point, (or if fax to provider had already been attempted), the Resolution Engine will either route to the store at step 250 or route to the resolution center at step 251 if the store is supported. From this point, pre-authorization will have to be obtained likely via phone call to the provider by an agent or pharmacy employee.

Figure 16:
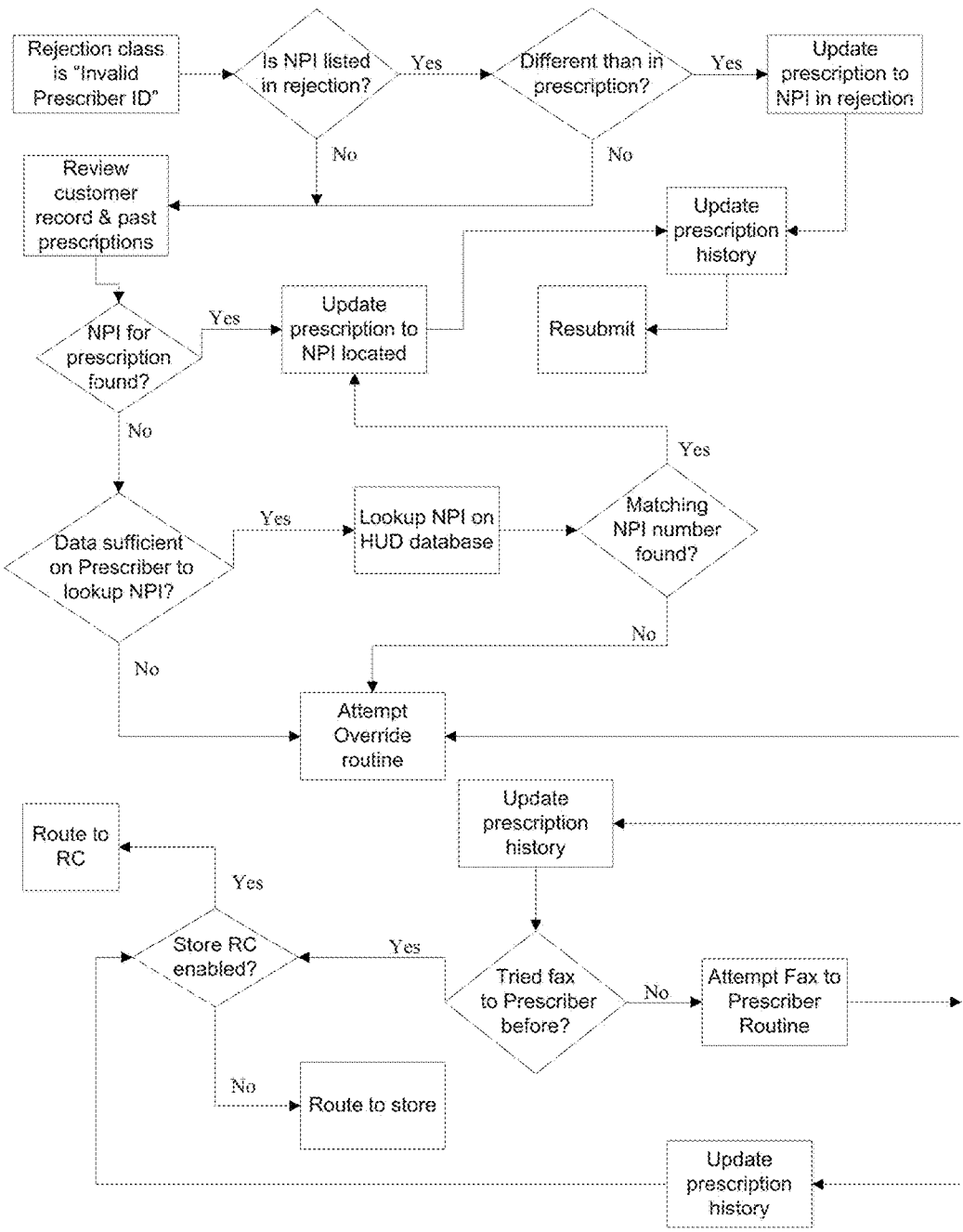
FIG. 16 is a flow chart showing steps performed by the resolution engine when a rejection is categorized as a mistake with the prescriber identification, in accordance with certain embodiments.

FIG. 16 provides an embodiment for a routine of the Resolution Engine where a rejection arrives at step 1600 with a category of "invalid prescriber identification." This category usually indicates that the payer does not recognize the prescribing physician. Some payers will not make this check and will accept prescriptions from any provider. Others at least verify that the NPI number for the provider matches information in the NPI database. Still others have "in network" rules, and will only accept prescriptions from certain providers.

In accordance with FIG. 16, the Resolution Engine starts by assuming a mistake in the provider identification and tries to correct it. If a correction to the provider identification is offered within the rejection messages the Engine updates the prescription to the offered/correct identification at step 1610, updates the prescription history at step 235 and resubmits at step 240. If not such identification is offered in the rejection, or that which is offered was what was already submitted, the system will review the customer history database to see if the proper provider information can be found from past prescriptions. The system will not simply change the provider, rather it is looking for mere data errors. For example, if a Dr. Muraff has been used for some time as the prescribing physician for drug X, but this time the drug is being prescribed by a Dr. Muraf with the same prescriber number, the system will determine this to be a typographical error, will correct and resubmit. But if the prescription is from a Dr. Murphy, having a different prescriber number, the system will not switch it back to Dr. Muraff.

If the proper prescriber identification (e.g., grammatical error) is found by reviewing the customer record, the prescription will be updated at step 1630 to reflect this, and the prescription will be resubmitted at step 240. If not, the system will try to look up the proper prescriber identification if sufficient information on the prescriber is provided within the prescription or rejection messages. This lookup is performed, for example, using the NPI database at step 1640. If the proper prescriber information is found, the prescription is updated at step 1630, the prescription history is updated at step 235, and the prescription is resubmitted at step 240. Otherwise, the Resolution Engine will have failed to find the proper prescriber identification on its own.

The next step is to attempt the Override subroutine at step 1609. If this succeeds, the prescription will be resubmitted from that subroutine. If not, flow will return and the prescription history will be updated at step 235. The next step is to attempt the Fax to Provider subroutine at step 1608, assuming this has not previously been attempted. Naturally the prescriber will know their own identification and can fix the problem. However, it is quite possible that there is no fax number or an incorrect fax number in these scenarios. Thus, if the Fax to Provider subroutine fails, flow will return, the prescription history will be updated at step 235, and the rejection will be routed based on whether or not the store is supported by the resolution center, as indicated.

Figure 17:
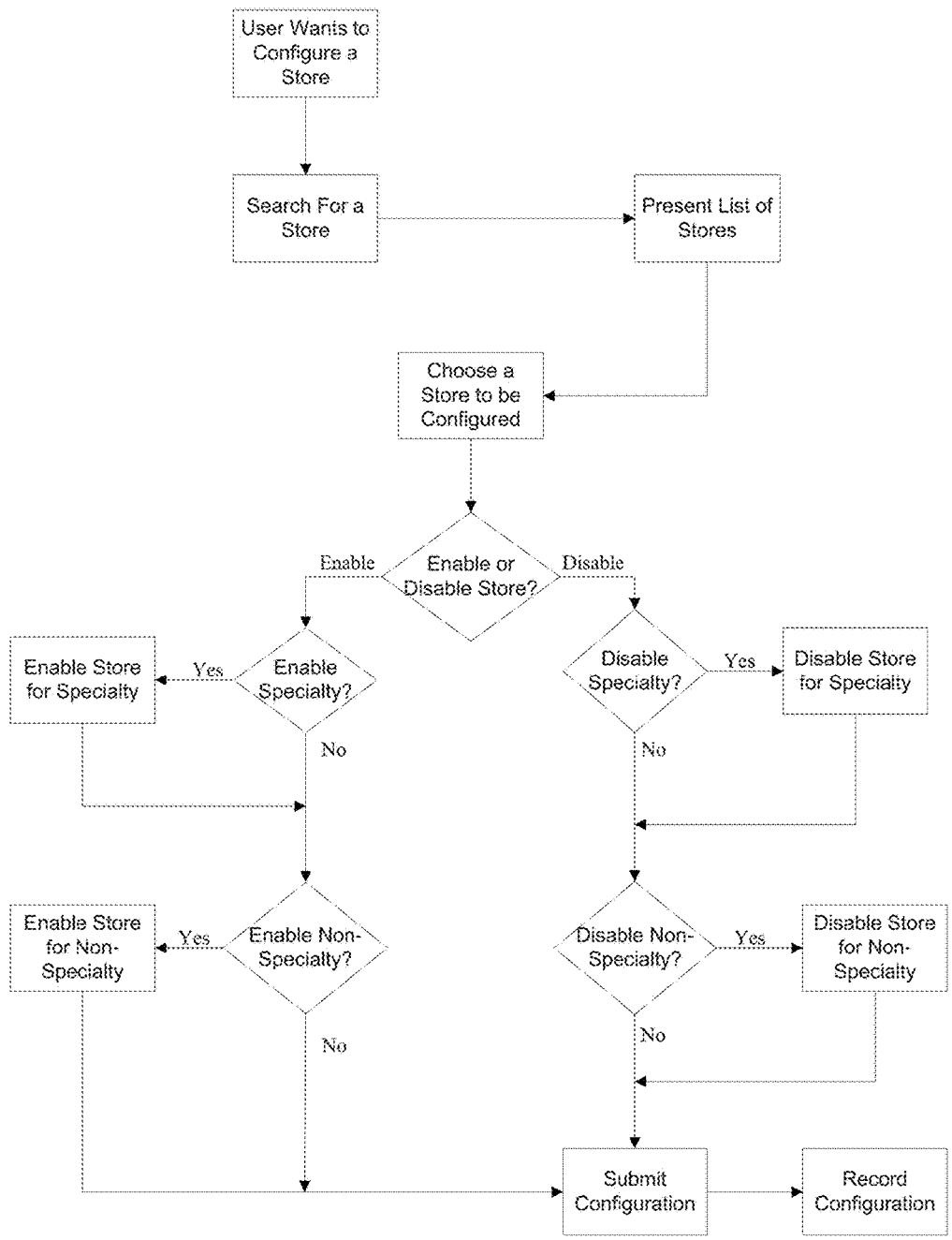
FIG. 17 is a flow chart showing steps performed by a system administrator or pharmacy manager to enable or disable features of the prescription approval system for individual stores, in accordance with certain embodiments.

Throughout the above-discussed scenarios, we have indicated several options that a store may independently set. For example, a store may decide what the threshold amount is where a prescription is simply billed directly to the customer, or a store may decide how many passes through the PAS is appropriate for its clientele under certain scenarios. FIG. 17 gives an example of how pharmacy personnel can interact with the PAS at an administrator level to configure options within how the PAS operates for the individual pharmacy. At step 1700, an administrator logs on to the PAS and searches for a store at step 1710. This would be using an interface on the store computer 190 presented by the central PAS server 162 via the internet, for example. The interface would provide a list of stores at step 1720 from which the administrator chooses the one to be configured at step 1730. This assumes that the administrator is authorized to change the configurations for the store.

The example of FIG. 17 shows the process used to enable or disable the store for allowing the PAS to work with designated "specialty" medications (steps 1740/1750), and for non-specialty medications (1760/1770), however it will be understood that other options could also be selected in this same scheme, such as, for example, the iterative procedures that the PAS should use when handling a rejection of a prescription submitted through the store in question. At step 1780, the new configuration is submitted to the PAS, where it is stored at step 1790 in the Pharmacy database component of the PAS database 160. In general, using a method such as this, a store administrator can completely disable or enable use of the PAS for the store, can add or delete payers for a customer record and update customer information, can set threshold pricing under which the customer will pay the bill outright, can set the number of months the PAS should look back in time to find information within the customer record, and may override a "regional setting" established by a higher level administrator for all stores within the region.

At a system level, an administrator of the PAS can create or edit logic rules governing resolution or categorization, can turn on or off rules for a specific region, specific payer, etc., can update or enter new fax templates for selection by the system, can update databases available to the PAS, and various other system level changes.

As the PAS is increasingly used, and as the empirical information grows in the PAS database, fewer rejections will occur and fewer steps will need to be taken to overcome those rejections because the system can rely on past success to determine rejection resolution. Also, prior to resubmission (from any routine or subroutine), the PAS can perform a review of the prescription using an error checking routine that allows it to predict whether a rejection will occur. Where the prediction is high, additional work may be performed prior to resubmission. The result of the resubmission will be recorded and figured into the checking routine to improve its accuracy for future submissions.

Figure 18:
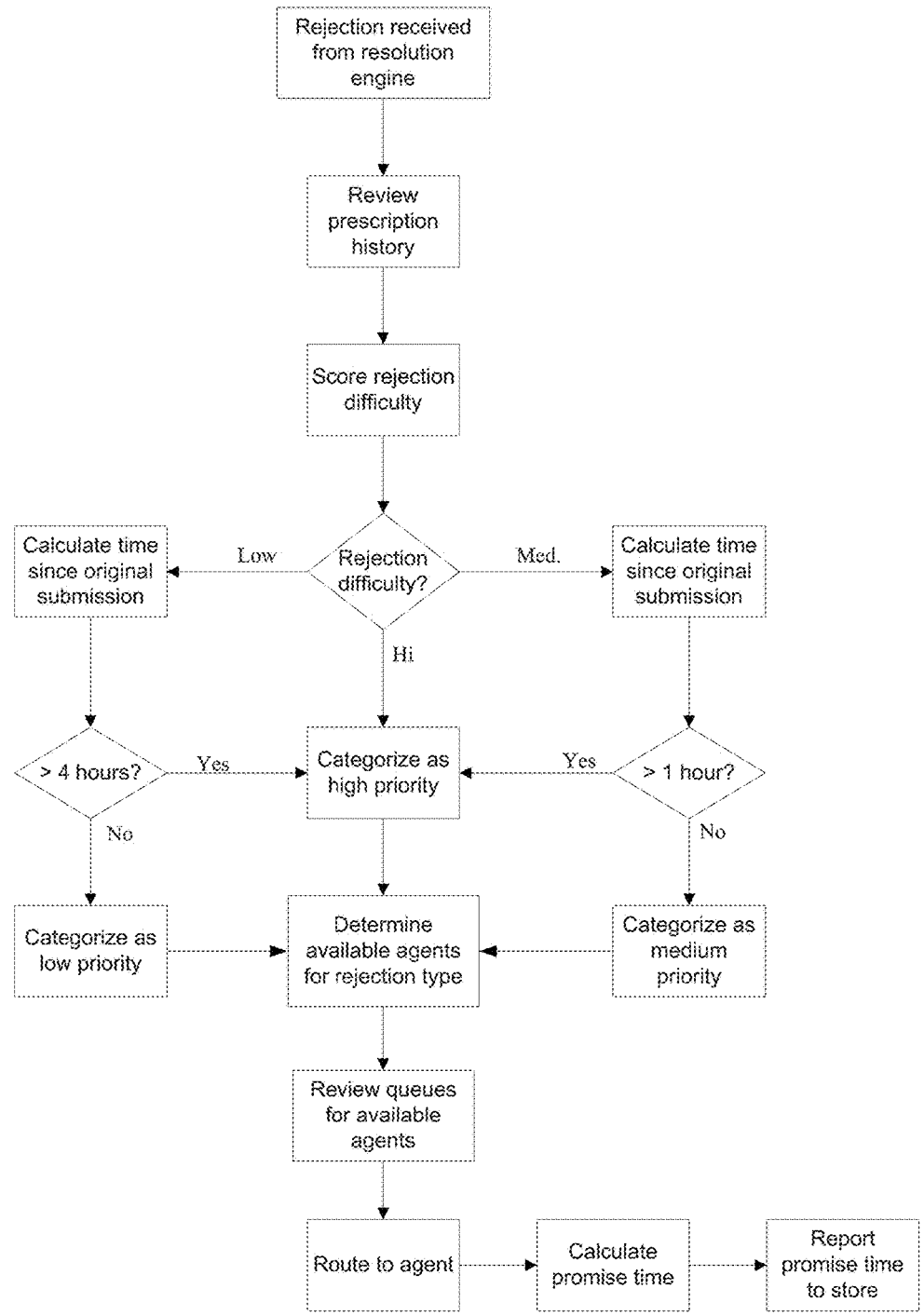
FIG. 18 illustrates a flow chart showing steps taken by the prioritization engine of the prescription approval system, in accordance with certain embodiments.

Turning to FIG. 18, an exemplary pathway is shown for how the PAS operates the Prioritization and Agent Matching Engines. This activity generally occurs prior to releasing an unresolved rejection from the Resolution Engine to the resolution center, in cases where a store is supported by the resolution center. Again, this generally is determined by the location of the store. Stores in states that do not require handling of prescriptions by in-state personnel will generally prefer to utilize the expertise and specialty skills of the resolution center.

At step 1800, the Prioritization Engine 330 receives the rejection and reviews the system-annotated prescription history at step 1810. Provided that the history has been properly updated by the Resolution Engine 320, this history will provide the Prioritization Engine 330 all of the information it needs to prioritize the rejection. First, it will identify when the prescription was first submitted by the pharmacy, and what attempts have been made to resolve the rejection since that time. As seen in FIG. 18, higher priority will be given to those prescriptions that have been waiting for a long time to be filled. The history will also inform as to the category of rejection. Some categories are known (based on system empirical data, agent-staffing, and otherwise) to be more time intensive and "difficult" for the resolution center to handle than others. The goal is to work through the more difficult rejections first, so as to prevent them from having long delivery times. Some categories take more time to research and others may require intensive paperwork. Meanwhile, others are easily resolved through a phone call, etc.

Once the prescription history has been reviewed, the Prioritization Engine 330 scores the perceived difficulty of the rejection at step 1820. Here, "difficulty" correlates to the estimated amount of time it is expected for an agent to take addressing the rejection. Once again, this typically is based on the rejection category, and a review of what has already been tried by the Resolution Engine 320. It also may depend on the location of the store, because some states have more requirements than others, or the resolution center may be more used to dealing with the rules of some states than others that must be reviewed. It is also considered more difficult when the prescription and rejection information is thin and some investigation will need to be done. Where this information is too thin, it may be most efficient for the resolution center to route the rejection back to the store for local investigation to gather further inputs.

As indicated in the exemplary embodiment, the priorities of high, medium and low difficulty may be used, though other priority levels, or numbers of levels could be used instead. If the difficulty is perceived as high, it is designated as high priority at step 1840. If the difficulty is perceived to be low or medium, there is an opportunity for the Prioritization Engine 330 to still designate the rejection as high priority based on the time since submission. Accordingly, at step 1830, the Prioritization Engine calculates the time since submission. If the difficulty was deemed low, but the prescription was originally submitted over four hours previously, the priority is switched to high. Otherwise the priority is designated as low at step 1860. If the difficulty was deemed medium, but the prescription was originally submitted over one hour previously, the priority is switched to high. Otherwise the priority is designated as medium at step 1850.

Figure 19:
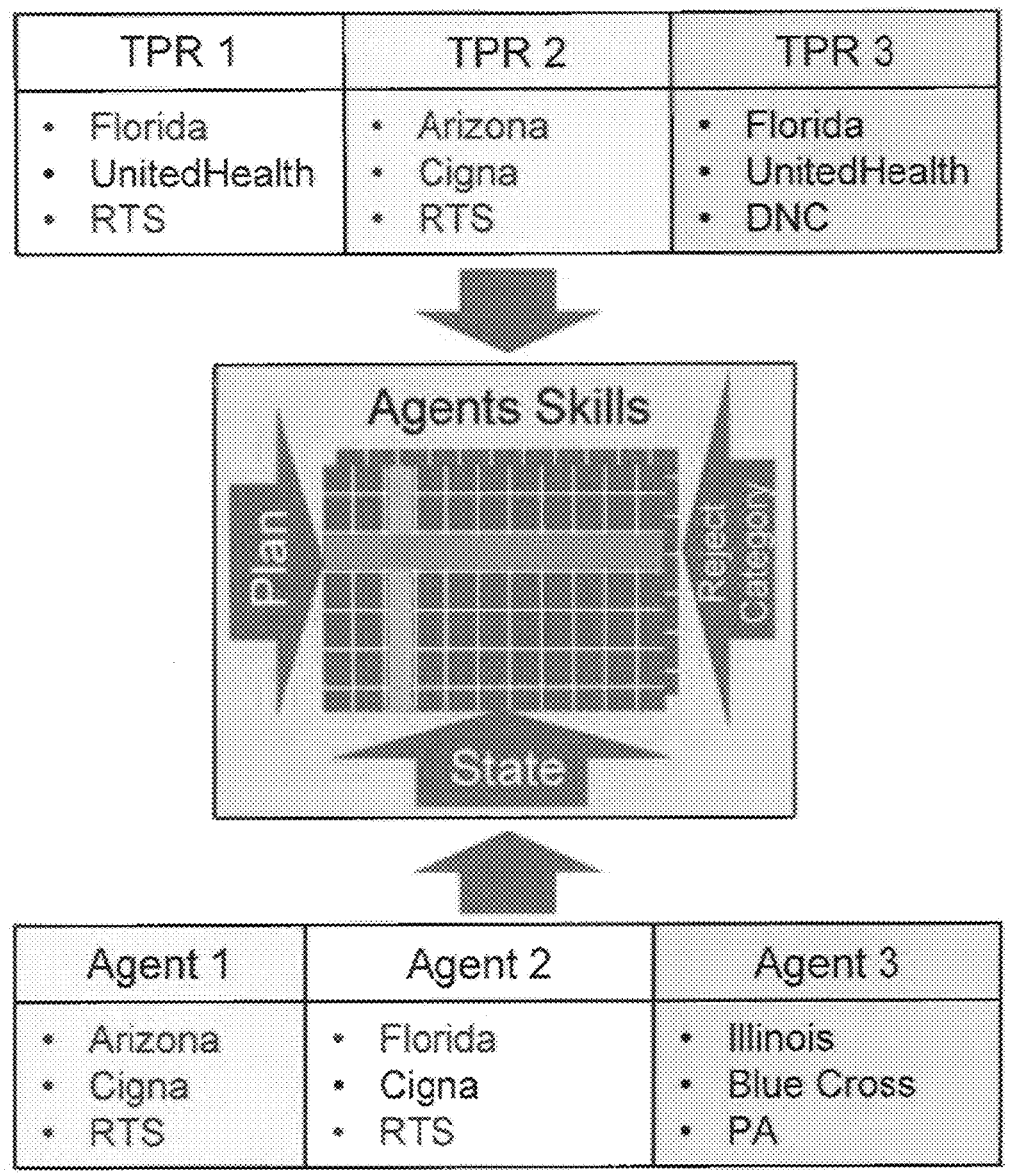
FIG. 19 is an exemplary mapping of options available to the agent matching engine of the prescription approval system, in accordance with certain embodiments.

Once the priority is set by the Prioritization Engine 330, the Agent Matching Engine 340 receives the rejection and places it in an agent's queue. In order to create further efficiency within the resolution center, agents specialize in particular categories of rejection, and may also specialize as to specific large payers, or specific states. Because the prescription rules vary by state and by payer, this specialization reduces the amount of research time that might otherwise need to occur when an agent comes across a rejection they are not familiar with. As shown in FIG. 19, the example forms a matrix relationship with three potential incoming rejections and three potential available agents. In this case each rejection is identified by (1) the state in which the filling store is located; (2) the name of the payer; and (3) the category of rejection (where "RTS"="refill too soon", for example). Shown below are three agents specializing in similar areas. The agent matching engine will take all of these things into account in matching the rejections to agents. While there may not always be perfect alignment like in the case of Rejection 2 and Agent 1, it would be better to place Rejection 1 with Agent 2 where the state and rejection category are in common, for example, than with Agent 3 where nothing is in common. Whether to place Rejection 3 with Agent 3 or set it in queue behind Agent 2 who is at least familiar with the state will depend on various availability and priority factors.

Returning to FIG. 18, at step 1870, the Agent Matching Engine must first determine what agents are available to handle the rejection. This does not mean the agent needs to be standing by waiting, but they must at least be on duty. The Engine 340 then takes into account the queues for the available agents at step 1880. Even where an agent profile matches a rejection type and prescription summary perfectly, the match may not be made where the agent in question has a full queue and others are standing by waiting for a rejection to work. Based on agents available, agent queues, rejection type, payer, state and priority of the rejection, the Agent Matching Engine selects a particular agent at step 1885. It then calculates a "promise time" at step 1890 that is reported by the PAS to the store at step 1895. The "promise time" is a factor of the agent's queue and the perceived difficulty of the rejection.

Once the agent addresses the rejection, an update is made to the prescription history and the rejection is resubmitted. In cases where the resolution center cannot resolve a rejection in sufficient fashion for resubmission, the rejection is returned to the store with instructions to bill the client the full amount.

It has thus been described how the PAS 100 can be implemented to facilitate the automated categorization, research, correction, enhancement, and resubmission of payment rejections for prescriptions. Any process descriptions or blocks in figures, such as FIGS. 7-16, should be understood as representing modules, segments, or portions of code which include one or more executable instructions for implementing specific logical functions or steps in the process. Certain process steps may be executed out of order from that shown or discussed, additional steps may be included, or some steps discussed may be bypassed or not used, without departing from the scope of the invention as disclosed, as would be understood by those having ordinary skill in the art.

It should be emphasized that the above-described embodiments of the present invention, particularly, any "preferred" embodiments, are possible examples of implementations, merely set forth for a clear understanding of the principles of the invention. Many variations and modifications may be made to the above-described embodiment(s) of the invention without substantially departing from the spirit and principles of the invention.

The invention claimed is:

1. A prescription approval system for automatically researching, correcting, and resubmitting a rejection of a prescription by a payer comprising:
   a first payer server for generating the rejection of the prescription;
   a prescription approval system database configured to store data for the prescription and a summary of historical actions taken by the prescription approval system to categorize previously-rejected prescriptions and resolution steps that have been previously performed to modify and resubmit the previously-rejected categorized prescriptions; and
   a prescription approval system server for receiving the rejection from the first payer server, the prescription approval system server, comprising:
      a categorization engine for assessing the rejection to categorize the rejection into a rejection category indicative of resolution steps to be taken based upon an inferential analysis that learns over time as additional prescriptions are rejected utilizing the summary of historical actions stored in the prescription approval system database;
      a resolution engine configured to resolve the categorized rejection by executing the resolution steps to modify and resubmit the prescription to either of the first payer server or a second payer server based upon an inferential analysis that learns over time as additional prescriptions are rejected utilizing the summary of historical actions stored in the prescription approval system database;
      a prioritization engine that, when the resolution engine fails to resolve the rejection, is configured to assign the rejection (i) a score in accordance with a perceived difficulty that is based upon attempts to resolve the categorized rejection made by the resolution engine since the prescription was originally submitted, wherein the perceived difficulty is correlated to a time expected for an agent to address the rejection, and wherein the time expected for an agent to address the rejection is based on one or more of:

the category associated with the rejection, a location associated with the rejection, or an amount of information associated with the rejection, (ii) a time priority for the rejection, wherein the time priority is based on an update frequency assigned to the prescription, a demanding customer, or urgent medical needs, and (iii) a priority based upon the score and the time priority; and an agent matching engine configured to assign the rejection to a particular agent based upon (i) the priority of the rejection assigned by the prioritization engine, and (ii) the category of rejection assigned by the categorization engine.

2. The prescription approval system of claim 1, wherein the reject category indicates the payer has rejected the prescription for at least one of the following reasons: (i) prescribing too many days of supply of a medication, (ii) the prescription being submitted before refill of a prescribed medication is timely, (iii) prescribing a medication not covered by the payer, (iv) a customer identified in the prescription not being covered by the payer (v) the prescription prescribing a medication requiring pre-approval that is lacking, and (vi) having an unrecognized prescriber identification.

3. The prescription approval system of claim 1, wherein the resolution engine, based on a response to execution of the resolution steps, is further configured to execute a subroutine.

4. The prescription approval system of claim 3, wherein the resolution engine is further configured to generate and send a facsimile in response to execution of the subroutine.

5. The prescription approval system of claim 3, wherein the resolution engine is further configured to submit the prescription to the second payer server in response to execution of the subroutine.

6. The prescription approval system of claim 3, wherein the resolution engine is further configured to submit an override request to the first payer server in response to execution of the subroutine.

7. The prescription approval system of claim 1, wherein the resolution engine, based on an insufficient amount of prescription and rejection information, is further configured to route the rejection back to an originating pharmacy for the prescription.

8. The prescription approval system of claim 1, wherein the prioritization engine is further configured to assign the priority to the rejection based upon a time when the prescription was originally submitted.

9. A prescription approval system implemented across a plurality of pharmacies, each pharmacy having at least one prescription entry device connected to a central prescription approval system server, the central prescription approval system server being further connected to a plurality of payer servers, and each payer server being associated with a separate payer entity, the prescription approval system comprising:

a prescription approval system database configured to store data for the prescription and a summary of historical actions taken by the prescription approval system to categorize previously-rejected prescriptions and resolution steps that have been previously performed to modify and resubmit the previously-rejected categorized prescriptions;

a categorization engine operated by the central prescription approval system server configured to (i) receive a rejection of a prescription from a payer server from among the plurality of payer servers, the rejection comprising a rejection code and message content for assessing the rejection, and (ii) categorize the rejection into a rejection category indicative of resolution steps to be taken based upon an inferential analysis that learns over time as additional prescriptions are rejected utilizing the summary of historical actions stored in the prescription approval system database;

a resolution engine operated by the central prescription approval system server, the resolution engine configured to resolve the categorized rejection by executing automated steps to correct the rejection and to modify and resubmit the prescription to one of the plurality payer servers based upon an inferential analysis that learns over time as additional prescriptions are rejected utilizing the summary of historical actions stored in the prescription approval system database, a prioritization engine operated by the central prescription approval system server, the prioritization engine configured to, when the resolution engine fails to resolve the rejection, assign to the rejection (i) a score in accordance with a perceived difficulty that is based upon attempts to resolve the categorized rejection made by the resolution engine since the prescription was originally submitted, wherein the perceived difficulty is correlated to a time expected for an agent to address the rejection, and wherein the time expected for an agent to address the rejection is based on one or more of: the category associated with the rejection, a location associated with the rejection, or an amount of information associated with the rejection, (ii) a time priority for the rejection, wherein the time priority is based on a certain amount of time passing since the prescription was first submitted, an update frequency assigned to the prescription, a demanding customer, or urgent medical needs, and (iii) a priority based upon the score and the time priority when the attempt to resolve the rejection via the resolution engine is not successful; and an agent matching engine operated by the central prescription approval system server, the agent matching engine configured to assign the rejection to a particular agent based upon (i) the priority of the rejection assigned by the prioritization engine, and (ii) the category of rejection assigned by the categorization engine, wherein the automated steps depend on a rejection category selected by the categorization engine.

10. The prescription approval system of claim 9, wherein the resolution engine is further configured to obtain first information about the prescription based on the message content and use the first information to modify the prescription.

11. The prescription approval system of claim 10, wherein the resolution engine is further configured to obtain the first information from a third party server.

12. The prescription approval system of claim 9, wherein the rejection code is different than the rejection category selected by the categorization engine.

13. The prescription approval system of claim 9, wherein the categorization engine is further configured to access the prescription approval system database to review steps previously taken by the resolution engine and, if the prescription has been rejected for more than a preset number of times, causes the prescription to bypass the resolution engine.

14. The prescription approval system of claim 13, wherein each pharmacy from among the plurality of pharmacies designates the preset number that is to apply to prescriptions that each pharmacy from among the plurality of pharmacies initially submits.

15. The prescription approval system of claim 9, wherein the prioritization engine is further configured to assign the priority to the rejection based upon a time when the prescription was originally submitted.

16. A computer-implemented method in a prescription approval system for automatically researching, correcting, and submitting a rejection of a prescription by a payer comprising:
  storing, by a prescription approval system database, data for the prescription and a summary of historical actions taken by the prescription approval system to categorize previously-rejected prescriptions and resolution steps that have been previously performed to modify and resubmit the previously-rejected categorized prescriptions;
  generating, by a first payer server, the rejection of the prescription;
  receiving, by a prescription approval system server, the rejection from the first payer server;
  assessing, by a categorization engine, the rejection to categorize the rejection into a rejection category indicative of resolution steps to be taken based upon an inferential analysis that learns over time as additional prescriptions are rejected utilizing the summary of historical actions stored in the prescription approval system database;
  attempting to resolve the categorized rejection by executing, via a resolution engine, the resolution steps to modify and resubmit the prescription to either the first payer server or a second payer server based upon an inferential analysis that learns over time as additional prescriptions are rejected utilizing the summary of historical actions stored in the prescription approval system database;
  assigning to the rejection, by a prioritization engine when the attempt to resolve the rejection via the resolution engine is not successful, (i) a score in accordance with a perceived difficulty that is based upon attempts to resolve the categorized rejection made by the resolution engine since the prescription was originally submitted, wherein the perceived difficulty is correlated to a time expected for an agent to address the rejection, and wherein the time expected for an agent to address the rejection is based on one or more of: the category associated with the rejection, a location associated with the rejection, or an amount of information associated with the rejection, (ii) a time priority for the rejection, wherein the time priority is based on a certain amount of time passing since the prescription was first submitted, an update frequency assigned to the prescription, a demanding customer, or urgent medical needs, and (iii) a priority based upon the score and the time priority when the attempt to resolve the rejection via the resolution engine is not successful; and
  assigning the rejection, by an agent matching engine, to a particular agent based upon (i) the priority of the rejection assigned by the prioritization engine, and (ii) the category of rejection assigned by the categorization engine.

17. The computer implemented method of claim 16, wherein the reject category indicates the payer has rejected the prescription for at least one of the following reasons: (i) prescribing too many days of supply of a medication, (ii) the prescription being submitted before refill of a prescribed medication is timely, (iii) prescribing a medication not covered by the payer, (iv) a customer identified in the prescription not being covered by the payer (v) the prescription prescribing a medication requiring pre-approval that is lacking, or (vi) having an unrecognized prescriber identification.

18. The computer-implemented method of claim 16, further comprising:
  recognizing, by the resolution engine, a need to execute a subroutine based upon a response to the execution of the resolution steps.

19. The computer-implemented method of claim 18, wherein the act of recognizing the need to execute the subroutine includes at least one of: (i) generating and sending a facsimile, (ii) submitting the prescription to the second payer server, and (iii) submitting an override request to the first payer server.

20. The computer-implemented method of claim 16, wherein the act of assigning the rejection to a particular agent further comprises:
  assigning the priority to the rejection based upon a time when the prescription was originally submitted.

* * * * *